US005656422A

United States Patent [19]
Crawford et al.

[11] Patent Number: 5,656,422
[45] Date of Patent: Aug. 12, 1997

[54] COMPOSITIONS AND METHODS FOR DETECTION OF 2,4-DICHLOROPHENOXYACETIC ACID AND RELATED COMPOUNDS

[75] Inventors: Ronald L. Crawford; Yongxiang Gu; Roger A. Korus; David B. Knaebel, all of Moscow, Id.

[73] Assignee: Idaho Research Foundation, Inc., Moscow, Id.

[21] Appl. No.: 318,505

[22] Filed: Oct. 5, 1994

[51] Int. Cl.$^6$ .................. C12Q 1/00; C12Q 1/26; C12N 5/00

[52] U.S. Cl. .................. 435/4; 435/25; 435/42; 435/46; 435/810; 435/822; 435/829; 435/849; 435/174; 435/177; 435/179; 435/180; 435/325; 435/349; 435/348; 435/419; 435/365; 435/367; 435/358

[58] Field of Search .................. 435/4, 25, 240.4, 435/240.1, 42, 46, 810, 822, 829, 849

[56] References Cited

PUBLICATIONS

Amy et al., "Characterization of Aquatic Bacteria and Cloning of Genes Specifying Partial Degradation of 2,4-Dichlorophenoxyacetic Acid," *Appl. Environ. Microbiol.* 49:1237–1245 (1985).

Chaudhry et al., "Flavobacterium sp. Which Carries the Genes for Degradation of 2,4-Dichlorophenoxyacetate," *J. Bacteriol.*, 170:3897–3902 (1988).

Danganan et al., "Nucleotide Sequence and Functional Analysis of the Genes Encoding 2,4,5-Trichlorophenoxyacetic Acid Oxygenase in Pseudomonas cepacia AC1100," *Appl. Environ. Microbiol.*, 60:4100–4106 (1994).

Daugherty et al., "Degradation of 2,4-Dichlorophenoxyacetic Acid by Pseudomonas cepacia DB01(pR0101) in a Dual-Substrate Chemostat," *Appl. Environ. Microbiol.*, 60:3261–3267 (1994).

Don et al., "Properties of Six Pesticide Degradation Plasmids Isolated from Alcaligenes paradoxus and Alcaligenes eutrophus," *J. Bacteriol.*, 145:681–686 (1981).

Don et al., "Transposon Mutagenesis and Cloning Analysis of the Pathways for Degradation of 2,4-Dichlorophenoxyacetic Acid and 3-Chlorobenzoate in Alcaligenes eutrophus JMP134(pJP4)," *J. Bacteriol.*, 161:85–90 (1985).

Don et al., "Genetic and Physical Map of the 2,4-Dichlorophenoxyacetic Acid–Degradative Plasmid pJP4," *J. Bacteriol.*, 161:466–468 (1985).

Donnelly et al., "Degradation of Atrazine and 2,4-Dichlorophenoxyacetic Acid by Mycorrhizal Fungi at Three Nitrogen Concentrations In Vitro," *Appl. Environ. Microbiol.*, 59:2642–2647 (1993).

Fukumori et al., "Alcaligenes eutrophus JMP134 '2,4-Dichlorophenoxyacetate Monooxygenase' Is an α-Ketoglutarate-Dependent Dioxygenase," *J. Bacteriol.*, 175:2083–2086 (1993).

Harker et al., "Phenoxyacetic Acid Degradation by the 2,4-Dichlorophenoxyacetic Acid (TFD) Pathway of Plasmid pJP4: Mapping and Characterization of the TFD Regulatory Gene, tfdR," *J. Bacteriol.*, 171:314–320 (1989).

(List continued on next page.)

*Primary Examiner*—John Kight
*Assistant Examiner*—Louise Leary
*Attorney, Agent, or Firm*—Klarquist Sparkman Campbell Leigh & Whinston

[57] ABSTRACT

Methods and compositions are provided for the detection of 2,4-dichlorophenoxyacetic acid (2,4-D) and other phenoxy ether compounds. The phenoxy ether bond of 2,4-D is enzymatically cleaved by 2,4-D α-ketoglutarate dioxygenase to form 2,4-dichlorophenol, which is assayed by the 4-aminoantipyrine method. The enzyme is supplied in a dried form, preferably immobilized on a solid support, and is stable at room temperature for several months even in a highly impure state, e.g., crude cell extracts or dried cells.

36 Claims, 22 Drawing Sheets

AMINOCARB (Matacil®)
4-(dimethylamino)-3-methylphenol methylcarbamate

PROPOXUR (Baygon®)
o-isopropoxyphenyl methylcarbamate

NAPROPAMIDE (Devrinol®)
2-(α-naphthoxy)-N,N-diethylpropionamide 2,4-D
(2,4-dichlorophenoxy)acetic acid 2,4,5-T
(2,4,5-trichlorophenoxy)acetic acid Silvex
2-(2,4,5-trichlorophenoxy)propionic acid CHLORONEB (Terraneb®)
1,4-dichloro-2,5-dimethoxybenzene DICAMBA (Banvel®)
2-methoxy-3,6-dichloro-benzoic acid FLUROXYPYR (Starane®)
[(4-amino-3,5-dichloro-6-fluoro-2-pyridinyl)oxy] acetic acid

OTHER PUBLICATIONS

Hultman, "Microbial Detoxification of Phenoxy Alkanoic Herbicide Containers and Rinseates," M.S. Thesis, University of Idaho, 89 pp. (1992).

Perkins et al., "Organization and Sequence Analysis of the 2,4-Dichlorophenol Hydroxylase and Dichlorocatechol Oxidative Operons of Plasmid pJP4," *J. Bacteriol.*, 172:2351–2359 (1990).

Short et al., "Effects of 2,4-Dichlorophenol, a Metabolite of a Genetically Engineered Bacterium, and 2,4-Dichlorophenoxyacetate on Some Microorganism-Mediated Ecological Processes in Soil," *App. Environ. Microbiol.*, 57:412–418 (1991).

Product literature regarding the 2,4-D RaPID Assay®, Ohmicron, Newton, Pennsylvania, 2pp.

Alexander, "Biodegradation and Bioremediation," Academic Press, p. 46.

Emerson et al., "The Condensation of Aminoantipyrine. II. A New Color Test for Phenolic Compounds; III. Reactions with Hydroxypyridines and Hydroxyquinolines; III. (1). The Synthesis of Methylrubazoic Acid; IV. (1). A Study of a New Color Reaction of Pyrazolons; VI. A Study of The Effect of Excess Base on the Reaction of Amino-Antipyrine with Phenolic Compounds in the Presence of Oxidizing Agents; VII. Hydrolysis in the Presence of Nitrous Acid (1)," *J. Org.Chem.*, 8:417–437; 532–537 (1943).

Kaphammer et al., "Cloning and Characterization of tfdS, the Repressor-Activator Gene of tfdB, from the 2,4-Dichlorophenoxyacetic Acid Catabolic Plasmid pJP4," *J. Bacteriol.*, 172:5856–5862 (1990).

Kaphammer et al., "Regulation of tfdCDEF by tfdR of the 2,4-Dichlorophenoxyacetic Acid Degradtion Plasmid pJP4," *J. Bacteriol.* 172:2280–2286 (1990).

Karns et al., "Regulation of 2,4,5-Trichlorophenoxyacetic Acid and Chlorophenol Metabolism in Pseudomonas cepacia AC1100," *Appl. Environm. Microbiol.*, 46:1182–1186 (1983).

Krueger et al., "Isolation and Identification of Microorganisms for the Degradation of Dicamba," *J. Agr. Food Chem.*, 37:534–538 (1989).

Krueger et al., "Use of Dicamba-Degrading Microorganisms to Protect Dicamba Susceptible Plant Species," *J. Agr. Food Chem.*, 39:1000–1003 (1991).

Lappin et al., "Degradation of the Herbicide Mecoprop [2-(2-Methyl-4-Chlorophenoxy) Propionic Acid] by a Synergistic Microbial Community," *Appl. Environ. Microbiol.*, 49:429–433 (1985).

Perkins et al., "Duplication of a 2,4-Dichlorophenoxyacetic Acid Monooxygenase Gene in Alcaligenes eutrophus JMP134(pJP4)," *J. Bacteriol.*, 170:5669–5672 (1988).

Streber et al., "Analysis, Cloning, and High-Level Expression of 2,4-Dichlorophenoxyacetate Monooxygenase Gene tfdA of Alcaligenes eutrophus JMP134," *J. Bacteriol.*, 169:2950–2955 (1987).

Tett et al., "Biochemistry of Mecoprop Degradation by AlCaligenes denitrificans," Abstract No. Q–85 of the General Meeting, American Society for Microbiology (1994).

Kilbane et al., "Biodegradation of 2,4,5-Trichlorophenoxyacetic Acid by a Pure Culture of Pseudomonas cepacia," *Appl. Environ. Microbiol.*, 44:72–78 (1982).

Pieper et al., "Metabolism of 2,4-Dichlorophenoxyacetic Acid, 4-Chloro-2-Methylphenoxyacetic Acid and 2-Methylphenoxyacetic Acid by Alcaligenes eutrophus JMP 134," *Arch. Microbiol.*, 150:95–102 (1988).

Kozyreva et al., "Metabolism of the Herbicide 2,4-D by a Nocardioides Simplex Strain," Plenum Publishing Corp., pp. 78–85 (1993), Institute of Biochemistry and Physiology of Microorganisms, Russian Academy of Sciences, Pushchino. Translated from Mikrobiologiya, vol. 62, No. 1, pp. 110–119, Jan.–Feb., 1993. Original article submitted Jul. 14, 1992.

Tiedje et al., "Enzymatic Cleavage of the Ether Bond of 2,4-Dichlorophenoxyacetate," *J. Agr. Food Chem.*, 17:1080–1084 (1969).

Bradley et al., "Biological Process for the Treatment of Water Contaminated with 2,4-Dichlorophenoxyacetic Acid (2,4-D)," Abstract No. Q–274 of the General Meeting, American Society for Microbiology (1994).

King et al., "Assay for Detection and Enumeration of Genetically Engineered Microorganisms Which is Based on the Activity of a Deregulated 2,4-Dichlorophenoxyacetate Monooxygenase," *Appl. Environ. Microbiol.*, 57:1790–1792 (Jun. 1991).

FIG. 1A

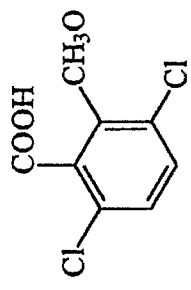
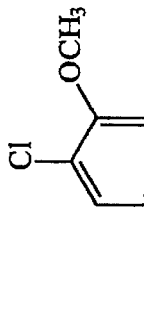
CHLORONEB (Terraneb®)
1,4-dichloro-2,5-dimethoxybenzene

2,4-D
(2,4-dichlorophenoxy)acetic acid

DICAMBA (Banvel®)
2-methoxy-3,6-dichloro-benzoic acid 2,4,5-T
(2,4,5-trichlorophenoxy)acetic acid

FLUROXYPYR (Starane®)
[(4-amino-3,5-dichloro-6-fluoro-2-pyridinyl)oxy] acetic acid Silvex
2-(2,4,5-trichlorophenoxy)propionic acid

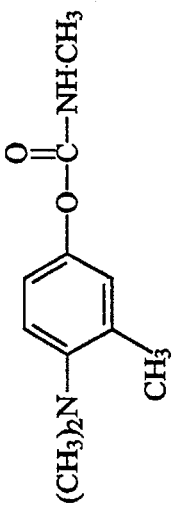
AMINOCARB (Matacil®)
4-(dimethylamino)-3-methylphenol methylcarbamate

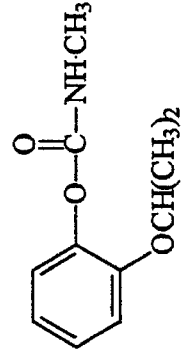
PROPOXUR (Baygon®)
o-isopropoxyphenyl methylcarbamate

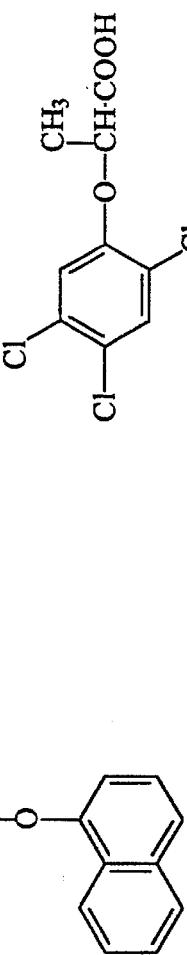
NAPROPAMIDE (Devrinol®)
2-(α-naphthoxy)-N,N-diethylpropionamide

FIG. 1B

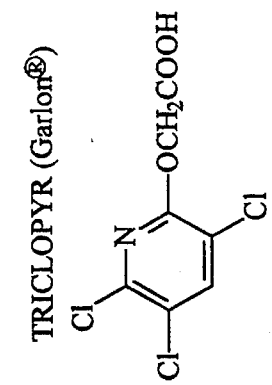
HALOXYFOP-METHYL (Verdict®, Gallant®)
(±)-2-[4-[[3-chloro-5-(trifluoromethyl)-2-pyridinyl]oxy] phenoxy]propanoic acid BINAPACRYL (Morocide®)
2-sec-butyl-4,6-dinitrophenyl 3-methyl-2-butenoate TRICLOPYR (Garlon®)
[(3,5,6-trichloro-2-pyridinyl) oxy] acetic acid MCPA
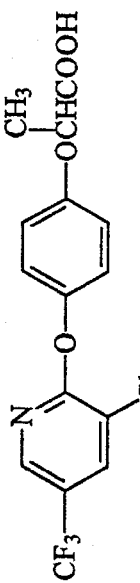
[(4-chloro-o-tolyl)oxy]acetic acid FENOXAPROP-ETHYL (Whip®)
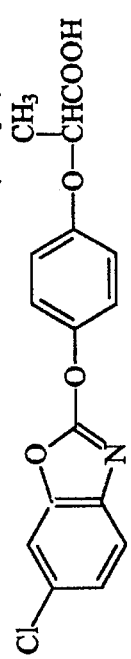
(±)-2-[4-[(6-chloro-2-benzoxazolyl)oxy]phenoxy] propanoic acid QUIZALOFOP-ETHYL (Assure®)
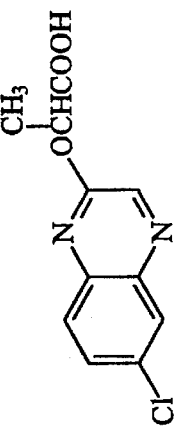
(±)-2-[4-(6-chloro-2-quinoxalinyloxy)phenoxy] propanoic acid BENDIOCARB (Ficam®, Turcam®)
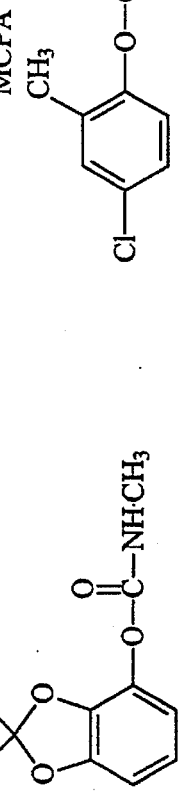
2,2-dimethyl-1,3-benzodioxol-4-yl methylcarbamate CARBOFURAN (Furadan®)
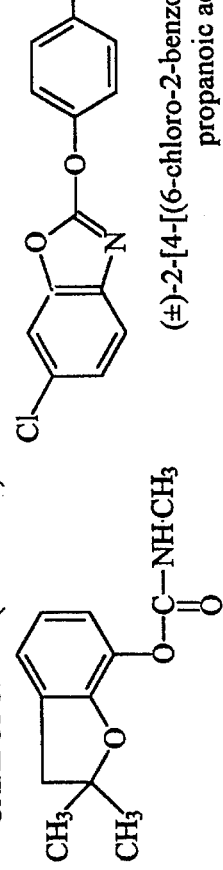
2,3-dihydro-2,2-dimethyl-7-benzofuranyl methylcarbamate CARBARYL (Sevin®)
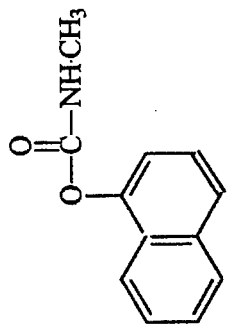
1-naphtyl methylcarbamate

FIG. 1C

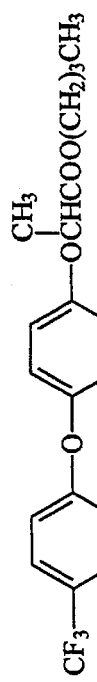
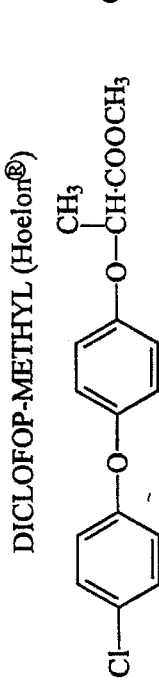
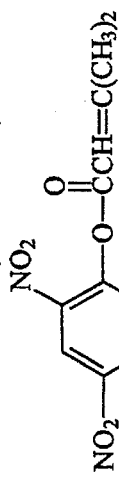
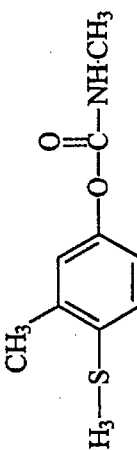
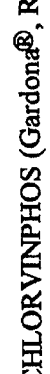
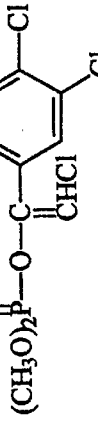
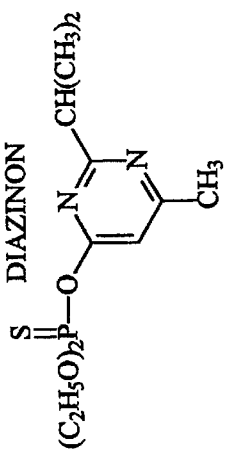
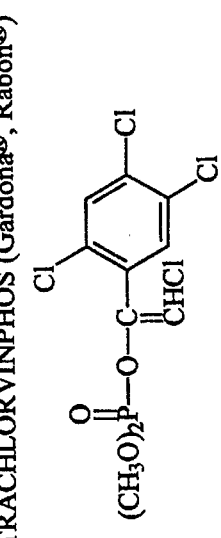

FLUAZIFOP-BUTYL (Fusilade®)
butyl 2-(4-(5-trifluoromethyl-2-pyridyloxy) phenoxy) propionate DICLOFOP-METHYL (Hoelon®)
2-(4-(2,4-dichlorophenoxy-phenoxy)-methyl-propanoate FENSON
p-chlorophenyl benzenesulfonate MEXACARBATE (Zectran®)
4-dimethylamino-3,5-xylyl N-methylcarbamate METHIOCARB (Mesurol®)
4-(methylthio)3,5-xylyl methylcarbamate DIAZINON
O,O-diethyl O-(2-isopropyl-4-methyl-6-pyrimidinyl) phosphorothioate DINOCAP (Karathane®)
2-(1-methylheptyl)-4,6-dinitrophenyl crotonate FORMETANATE (Carzol®)
[3-dimethylamino-(methylene-iminophenyl)-N-methylcarbamate hydrochloride TETRACHLORVINPHOS (Gardona®, Rabon®)
O,O-dimethyl O-2-chloro-1-(2,4,5-trichlorophenyl) vinyl phosphate

FIG. 1D

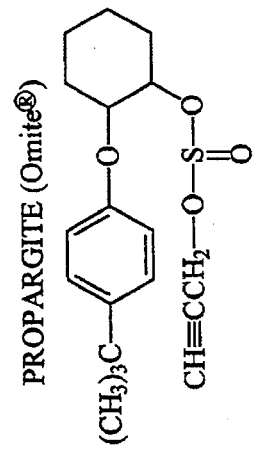

OVEX (Ovotran®)

*p*-chlorophenyl *p*-chlorobenzenesulfonate

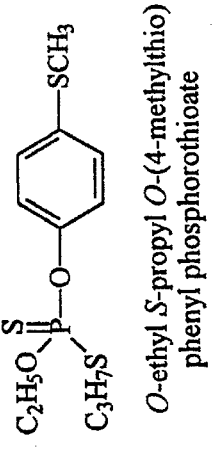

RONNEL (Korlan®)

*O,O*-dimethyl *O*-2,4,5-trichlorophenyl methylphosphorothioate

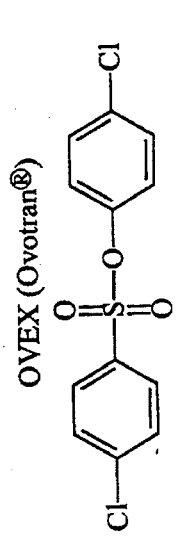

PROFENOFOS (Curacron®)

*O*-(4-bromo-2-chlorophenyl)-*O*-ethyl-*S*-propyl phosphorothioate

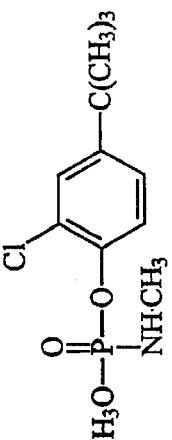

SULPROFOS (Bolstar®)

*O*-ethyl *S*-propyl *O*-(4-methylthio) phenyl phosphorothioate

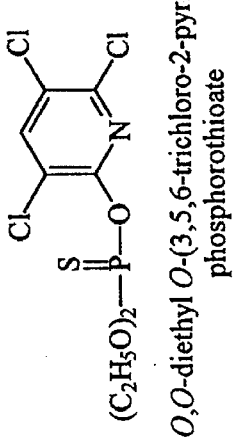

CHLORPYRIFOS (Dursban®, Lorsban®)

*O,O*-diethyl *O*-(3,5,6-trichloro-2-pyridyl) phosphorothioate

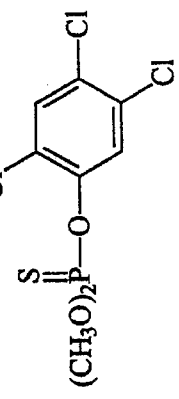

ISOFENPHOS (Amaze®, Pryfon®)

1-methylethyl 2-{[ethoxy (1-methyl-ethyl) amino phospinothioyl] oxy} benzoate

PROPARGITE (Omite®)

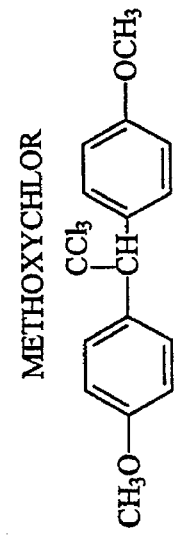

2-(*p*-tert-butylphenoxy)cyclohexyl 2-propynyl sulfite

CRUFOMATE (Ruelene®)

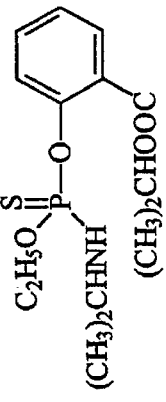

4-tert-butyl-2-chlorophenyl methyl-methylphosphoramidate

METHOXYCHLOR

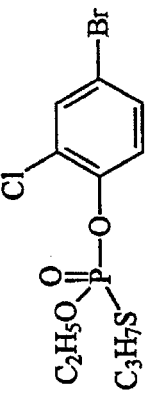

1,1,1-trichloro-2,2-bis(*p*-methoxyphenyl)ethane 5,656,422

COMPOSITIONS AND METHODS FOR DETECTION OF 2,4-DICHLOROPHENOXYACETIC ACID AND RELATED COMPOUNDS

ACKNOWLEDGMENT OF GOVERNMENT SUPPORT

This invention was made with government support under EPSCoR Grant No. OSR-9350539, awarded by the National Science Foundation, and contract AFOSR910315, awarded by the United States Air Force. The Government has certain rights in the invention.

TECHNICAL FIELD

This invention pertains to the field of methods for detection of biocides, i.e., herbicides and pesticides. More specifically, the invention is related to methods for the detection of 2,4-dichlorophenoxyacetic acid and related compounds.

BACKGROUND ART

Within the last 40–50 years, the use of biocides (herbicides and pesticides) has increased dramatically. Among these biocides are the chlorinated derivatives of phenoxyacetic acid (PAA). 2,4-Dichlorophenoxyacetic acid (2,4-D), introduced in 1944, was the first phenoxy herbicide and is possibly the most widely used herbicide (W. Evans et al., *J. Biochem.* 1971, 122, 543–551). Although 2,4-D is not highly toxic, cleanup of inadvertently spilled 2,4-D is still necessary (P. Amy et al., *Appl. Environ. Microbiol.* 1985, 49, 1237–1245; R. Beadle and A. Smith, *Eur. J. Biochem.* 1982, 123, 323–332; W. Evans et al., *J. Biochem.* 1971, 122, 543–551; P. Fisher et al., *Bacteriol.* 1978, 135, 793–804; L. Geer et al., *Appl. Environ. Microbiol.* 1992, 58, 1027–1030).

Although large amounts of 2,4-D are used each year, this herbicide usually does not accumulate in soil or water. Of the chlorinated phenoxy herbicides, it is less recalcitrant than more highly chlorinated compounds in the same herbicide class. 2,4-D is degraded naturally in soil under favorable environmental conditions by indigenous, competent microbial communities. There have been isolated from soil and water a number of organisms that are capable of degrading chlorinated phenoxy herbicides, such as 2,4-D, including a number of bacterial strains in multiple genera (L. Kozyreva et al., *Mikrobiologiya.* 1992, 62, 110–119; G. Chaudhry and G. Huang, *J. Bacteriol.* 1988, 170, 3897–3902; P. Amy et al., *App. Environ. Microbiol.* 1985, 49, 1237–1245; R. Don and J. Pemberton, *J. Bacteriol.* 1981, 145, 681–686; P. Fisher et al., *J. Bacteriol.* 1978, 135, 798–804; J. Tiedje et al., *J. Agr. Food Chem.* 1969, 17, 1021–1026; see also, Reineke and Knackmuss, *Ann. Rev. Microbiol.* 1988, 42, 263–287) and fungi (P. Donnelly et al., *App. Environ. Microbiol.* 1993, 59, 2642–2647

The best understood biochemical pathway for the microbial degradation of 2,4-D is that of *Alcaligenes eutrophus* JMP134 (R. Don and J. Pemberton, *J. Bacteriol.* 1981, 145, 681–686; R. Don et al., *J. Bacteriol.* 1985, 161, 85–90; R. Don and J. Pemberton, *J. Bacteriol.* 1985, 161, 466–468). In this pathway, 2,4-D is first converted by an α-ketoglutarate-dependent dioxygenase (the product of the tfdA gene) to 2,4-dichlorophenol and then by a DCP hydroxylase (the product of the tfdB gene) to 3,5-dichlorocathechol (DCCAT). After several additional enzymatic steps, chloromaleylacetic acid is finally produced (R. Don et al., *J. Bacteriol.* 1985, 161, 85–90; B. Kaphmmer and R. Olsen, *J. Bacteriol.* 1990, 172, 5856–5862). The genes encoding the enzyme responsible for the catabolism of 2,4-D by *A. eutrophus*, tfdA, tfdB and tfdCDEF, have been located on plasmid pJP4 (B. Kaphmmer and R. Olsen, *J. Bacteriol.* 1990, 172, 5856–5862; B. Kaphmmer et al., *J. Bacteriol.* 1990, 172, 2280–2286; E. Perkins and P. Lurquin, *J. Bacteriol.* 1988, 170, 5669–5672; W. Streber et al., *J. Bacteriol.* 1987, 169, 2950–2955). The expression of tfdB is regulated by the product of gene tfdS using 2,4-D and DCP as effectors (B. Kaphmmer and R. Olsen, *J. Bacteriol.* 1990, 172, 5856–5862). Since both 2,4-D and DCP can induce the expression of tfdB, DCP is further transformed by microorganisms bearing pJP4 or its derivatives, pRO101 or pRO103 (A. Harker et al., *J. Bacteriol.* 1989, 171, 314–320). No DCP can be detected by the color reaction in the culture media of these microorganisms when 2,4-D is supplied.

Analytical support for 2,4-D cleanup techniques usually involves gas-chromatography or high pressure liquid chromatography (HPLC) (see, e.g., K. Short et al., *App. Environ. Microbiol.* 1991, 57, 412–418) or immunoassays (e.g., the enzyme-linked immunosorbent assay [ELISA], 2,4-D RaPID Assay®, Ohmicron, Newtown, Pa.). Even the presently available immunoassays are relatively expensive. Therefore, it is important to develop quick, inexpensive, and easy-to-use 2,4-D detection methods for use in the field, particularly methods which can be employed by non-specialists. It would be particularly advantageous to develop an assay method which could be applied beyond 2,4-D to other related chemical compounds, particularly other phenoxy biocides, many of which are less easily degraded by naturally occurring organisms.

SUMMARY OF THE INVENTION

The present invention provides methods for detecting the presence of a phenoxy ether compound in a sample, the method comprising the steps of: providing a dried enzyme capable of cleaving a phenoxy ether bond of the compound to produce a phenolic product; hydrating the dried enzyme, thereby producing a hydrated enzyme; contacting the sample with the hydrated enzyme under conditions compatible with activity of the enzyme; and detecting the presence of the phenylic product, preferably by an assay comprising reacting the phenolic product with 4-aminoantipyrine and potassium ferricyanide.

The phenoxy ether compound to be detected by the methods of the present invention is preferably selected from the group consisting of: 2,4-dichlorophenoxyacetic acid (2,4-D) and its amine, ester, and other derivatives; 3,6-Dichloro-o-anisic acid (3,6-dichloro-2-methoxybenzoic acid (Dicamba, Banvel®) and its ester and other derivatives; 4-chloro-2-methyl-phenoxyacetic acid (MCPA); phenoxyacetic acid, 2-(2,4-dichlorophenoxy)propionic acid (2,4-DP) and its amine or ester derivatives; 2-(4-chloro-2-methylphenoxy)-propionic acid (MCPP) and its amine, ester, and other derivatives; (2,4,5,-trichlorophenoxy)acetic acid (2,4,5-T); 2,3-dihydro-2,2-dimethyl-7-benzofuranyl methylcarbamate (Carbofuran, Furadan®); p-chlorophenyl benzenesulfonate (Fenson); p-chlorophenyl p-clorobenzenesulfonate (Ovex, Ovotran®); 2-(p-tert-butylphenoxy)cyclohexyl 2-propynyl sulfite (Propargite, Omite®); 1-naphtyl methylcarbamate (Carbaryl, Sevin®); o,o-dimethyl o-2,4,5-trichlorophenyl methylphosphorothioate (Ronnel, Korian®); 4-tert-butyl-2-chlorophenyl methyl-methylphosphoroamidate (Crufomate, Ruelene®); o,o-dimethyl o-2-chloro-1-(2,4,5-trichlorophenyl) vinyl phosphate (Tetrachlorvinphos, Gardona®, Rabon®); o-(4-bromo-2-chlorophenyl)-o-ethyl-S-propyl phosphorothioate (Profenofos, Curacton®); o-ethyl S-propyl o-(4-methylthio) phenyl phosphorodithioate (Sulprofos, Bolstare); 1-methylethyl 2-([ethoxy (1-methyl-ethyl) amino phosphinothioyl] oxy)benzoate (Isofenphos, Amaze®, Pryfon®); o,o-diethyl o-(2-isopropyl-4-methyl-6-pyrimidinyl) phosphorothioate (Diazinon); o,o-diethyl o-(3, 5,6-trichloro-2-pyridyl) phosphorothioate (Chlorpyrifos, Dursban®, Lorsban®); 1,1,1-trichloro-2,2-bis(p-methoxyphenyl)ethane (Methoxychlor); butyl 2-(4-(5-trifluoromethyl-2-pyridyloxy)phenoxy) propionate (Fluazifop-butyl, Fusilade®); (±)-2-[4-[(6-chloro-2-benzoxazolyl)oxy]phenoxy]propanoic acid (Fenoxapropethyl, Whip®); 2-(4-(2,4-dichlorophenoxy-phenoxy)-methyl-propanoate (Diclofop methyl, Hoelon®); (±)-2-[4-(6-chloro-2-quinoxalinyloxy)phenoxy]propanoic acid (Quizalofop-ethyl, Assure®); 4-dimethylamino-3,5-zylyl N-methylcarbamate (Mexacarbate, Zectran®); 2-sec-butyl-4,6-dinitrophenyl 3-methyl-2-butenoate (Binapacryl, Morocide®); 2-(1-methylheptyl)-4,6-dinitrophenyl crotonate (Dinocap, Karathane®); 1-naphthyl N-methylcarbamate (Carbaryl, Sevin®); [(3,5,6-trichloro-2-pyridinyl)oxy]acetic acid (Triclopyr, Garlon®); [3-dimethylamino-(methylene-iminophenyl)]-N-methylcarbamate hydrochloride (Formetanate, Carzol®); 4-(methylthio)3,5-xylyl methylcarbamate (Methiocarb, Mesurol®); 4-(dimethylamino)-3-methylphenol methylcarbamate (Aminocarb, Matacil®); 2-(α-naphthoxy)-N,N-diethylpropionamide (Napropamide, Devrinol®); o-isopropoxyphenyl methylcarbamate (Propoxur, Baygon®); 2,2-dimethyl-1,3-benzo dioxol-4-yl methylcarbamate (Bendiocarb, Ficame, Turcam®); 2-(2,4,5-trichlorophenoxy)propionic acid (Silvex); [(4-chloro-o-tolyl)oxy]acetic acid (MCPA); Chloroneb; [(4-amino-3,5-dichloro-6-fluoro-2-pyridinyl)oxy] acetic acid (Fluroxypyr, Starane®); and (±)-2-[4-[[3-chloro-5-(trifluoromethyl)-2-pyridinyl]oxy] phenoxy]propanoic acid (Haloxyfop-methyl, Verdict®, Gallant®). Most preferably, the compound is a selected from the group consisting of 2,4-dichlorophenoxyacetic acid, amine derivatives of 2,4-dichlorophenoxyacetic acid, ester derivatives of 2,4-dichlorophenoxyacetic acid, 4-chloro-2-methyl-phenoxyacetic acid, 2-methylphenoxyacetic acid, and phenoxyacetic acid; most preferably, the compound is 2,4-dichlorophenoxyacetic acid, in which case the phenolic product is 2,4-dichlorophenol.

The dried enzyme employed in the practice of the methods of the present invention is preferably a 2,4-D α-ketoglutarate dioxygenase, which may be provided, for example, in the form of: a whole dried cell, preferably a cell in which is expressed a recombinant nucleic acid that encodes 2,4-D α-ketoglutarate dioxygenase, or a dried crude lysate of such a cell. Preferably, the dried enzyme (or cell or cell lysate) is immobilized on a solid support, such as a bead or dipstick.

For the detection of 3,6-dichloro-o-anisic acid and derivatives thereof, the dried enzyme is preferably a 2,6-dichloro-2-methoxy-benzoic acid mono-oxygenase.

The present invention also provides compositions for detecting the presence of a phenoxy ether compound in a sample, the compositions comprising a dried enzyme preparation, the preparation comprising an enzyme, preferably a 2,4-D α-ketoglutarate dioxygenase, that is capable when hydrated of cleaving a phenoxy ether bond of the compound to produce a phenolic product, immobilized on a solid support. The dried enzyme preparation may be, for example, a cell, preferably a cell comprising a recombinant nucleic acid that encodes the 2,4-D α-ketoglutarate dioxygenase, or a crude lysate of such a cell. The solid support is preferably a bead and a dipstick.

Also provided are kits for detecting the presence of a phenoxy ether compound in a sample, the kits comprising: a dried enzyme preparation comprising an enzyme, preferably a 2,4-D α-ketoglutarate dioxygenase, capable, when hydrated, of cleaving a phenoxy ether bond of the compound to produce a phenolic product under conditions compatible with activity of the enzyme; 4-aminoantipyrine; potassium ferricyanide; and instructions for use. Preferably, the kit further comprises $Fe(NH_4)_2(SO_4)_2$ and α-ketoglutarate. Again, the dried enzyme preparation may be, e.g., a cell, preferably a cell comprising a recombinant nucleic acid that encodes the 2,4-D α-ketoglutarate dioxygenase, or a crude lysate of such a cell, and is preferably immobilized on a solid support, e.g., a bead or a dipstick. In a preferred embodiment, a kit is provided comprising: an aqueous 5 mM $Fe(NH_4)_2(SO_4)_2$ solution; an aqueous 100 mM α-ketoglutarate solution; an aqueous 40 mM 4-aminoantipyrine solution; an aqueous 8% wt/vol potassium ferricyanide solution; an aqueous pH 8.0 buffer solution; and instructions for use.

BRIEF DESCRIPTION OF THE DRAWINGS

FIG. 1A, 1B, 1C and 1D shows chemical structures of a variety of compounds containing ethers linked to an aromatic ring.

MODES FOR CARRYING OUT THE INVENTION

Figure 2:
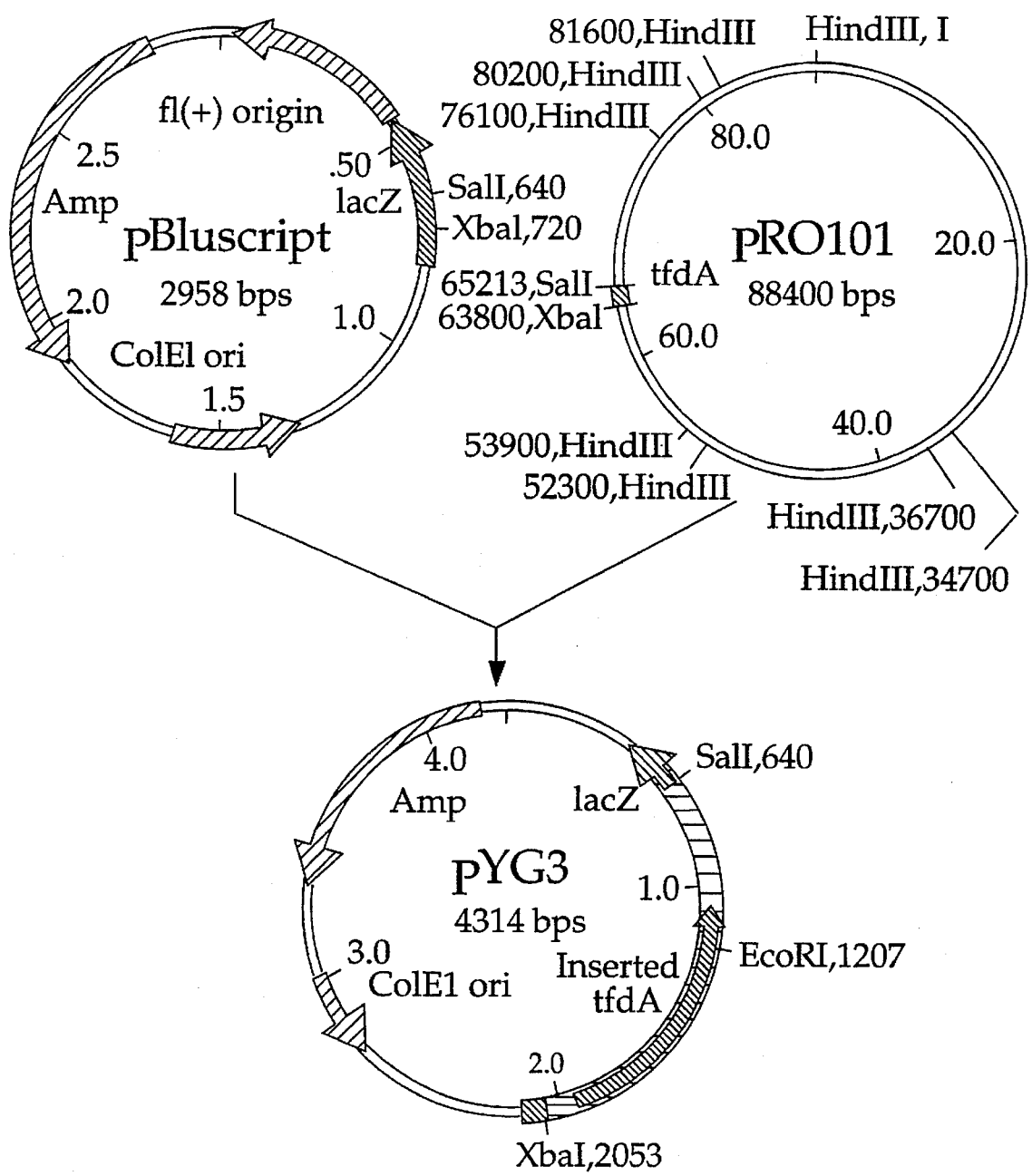
FIG. 2 shows the construction of pYG3 from pBluescript® SK+ and pRO101.

The present invention provides methods and compositions for the simple, inexpensive, and sensitive detection of 2,4-dichlorophenoxyacetic acid ("2,4-D") and other phenoxy ether compounds in test samples without using analytical equipment.

Briefly stated, the phenoxy ether bond of 2,4-D is enzymatically cleaved by 2,4-D α-ketoglutarate dioxygenase (DDO) to form a phenolic product, 2,4-dichlorophenol (DCP), which can be easily assayed with high sensitivity by the 4-aminoantipyrine method. The DDO is supplied in a dried form, preferably immobilized on a solid support. Even in a highly impure state, e.g., crude extracts of cells expressing recombinant DDO, DDO is stable at room temperature for several months, maintaining enzymatic activity and displaying an impressive sensitivity. The detection methods of the present invention are inexpensive, highly sensitive, and easy to use, even by untrained personnel in the field.

Enzymatic conversion of 2,4-D to DCP

An enzyme capable of transforming 2,4-D into DCP is found in all 2,4-D degrading microorganisms examined to date. However, in nature, DCP is itself quickly metabolized and does not accumulate. *Alcaligenes eutrophus* JMP134, for example, converts DCP to 3,5-dichlorocathechol (DCCAT) by a DCP hydroxylase (the product of the tfdB gene). This problem was overcome, however, by cloning and expressing the tfdA gene in *E. coli* DH5α (pYG3) and *Pseudomonas aeruginosa* PAO1 (pRO103), organisms that lack the capacity to metabolize DCP. Cell-free extracts of these recombinant organisms convert 2,4-D into DCP, which accumulates.

Even after storage at room temperature for several months, cell-free extracts prepared from the recombinant *E. coli* DH5α (pYG3) and air-dried on filter paper bags were capable of converting 2,4-D to DCP. The stability of air-dried DDO was unexpected. Many enzymes, particularly oxygenases, cannot be dried at ambient temperature without complete loss of enzymatic activity due to denaturation. Most enzymes are denatured rapidly at room temperature, even when dried. See, e.g., Fox et al., *J. Biol. Chem.* 1989, 264, 10023–10033; Nozake, Nonheme iron dioxygenases. In, O. Hayaishi (ed.), *Molecular Mechanisms of Oxygen Activation*. Academic Press: New York, 1974, pp. 135–165.

Moreover, it was discovered that air-dried DDO maintained its activity and displayed an impressive sensitivity even in an impure state. As shown in the Examples below, it was possible to detect 1–2 ppm of 2,4-D in a sample by visual inspection even when the enzyme was present in air-dried cells or crude cell-free extracts. Often it is necessary to purify such enzymes away from other cellular components, e.g., proteinases, before they can be stabilized sufficiently for commercial use. Therefore, according to the present invention, the enzyme used for detection of phenoxy ether compounds, e.g., DDO, may be provided in a purified form, as a partially purified product, or as a crude lysate (cell-free extract) or even as a whole cell.

Since the membrane of *E. coli* is not permeable to 2,4-D, if the enzyme is produced in *E. coli*, the enzyme should be provided in the form of a cell-free extract or more purified form, or, alternatively, the cells should be made permeable by means known in the art.

Cell-free extracts of the enzyme produced by recombinant means in *E. coli* may be easily prepared by passing the cells through a French press and clarifying the debris by centrifugation, or by other means well known in the art.

The enzyme can be produced by any of the recombinant expression systems known in the art, as well as by chemical synthesis. Recombinant expression has been studied extensively and optimized in *E. coli* DH5α (pYG3) and *P. aeruginosa* PAO1 (pRO103), as discussed in the Examples below.

The enzyme may be dried by any of the various means known in the art for drying cells or proteins, including (but not limited to) air drying, freeze drying (i.e., lyophilization), or vacuum drying, and compatible with retention of activity of the enzyme. The dried enzyme can be hydrated and thus reactivated by the addition of water or an aqueous solution, e.g., the aqueous sample to be tested.

Range of compounds detectable by the methods of the invention

The present invention can be used to detect the presence of a wide range of phenoxy compounds, many of which are commercially used biocides (herbicides or pesticides).

DDO is specific for 2,4-D. DDO can also be used to detect derivatized formulations of 2,4-D, including amine derivatives (e.g., 2,4-D dimethylamine, 2,4-D isopropylamine, 2,4-D triethylamine, 2,4-D diethanolamine, and 2,4-D triethanolamine) and ester derivatives (e.g., methyl, ethyl, propyl, etc.). In order to adapt the assay procedure described in the Examples below to the detection of such amine and ester derivatives, it may be necessary to add an initial hydrolysis step (addition of acid or base followed by readjustment to neutral pH, or an esterase enzyme) to convert the amine or ester form to the free acid.

Besides 2,4-D, DDO cleaves the side chain of 4-chloro-2-methyl-phenoxyacetic acid (MCPA), an important herbicide, to form 4-chloro-2-methylphenol, and cleaves 2-methylphenoxyacetic acid to yield 2-methylphenol (Pieper et al., *Arch. Microbiol.* 1988, 150, 95–102). DDO also cleaves the side chain of unchlorinated phenoxyacetic acid (Harker et al., *J. Bacteriol.* 1989, 171, 314–320).

A number of other phenoxy ether compounds may also be detected by the methods of the present invention. These compounds include:

1. 3,6-Dichloro-o-anisic acid (3,6-dichloro-2-methoxybenzoic acid (Dicamba, Banvel®) and its ester and other derivatives. The assay of Dicamba employs, instead of DDO, a demethylase, 3,6-dichloro-2-methoxybenzoic acid mono-oxygenase, that converts Dicamba to 3,6-dichloro-2-hydroxy-benzoic acid, a phenolic product that is assayed calorimetrically as in the 2,4-D assay.

Microbes are known which degrade Dicamba, including strains of Pseudomonas, Moraxelia, and Xanthomonas (Krueger et al. *J. Agr. Food Chem.*, 1989, 37, 534–538; Krueger et al., *J. Agr. Food Chem.* 1991, 39, 1000–1003). Since cleavage of aromatic methoxyls such as Dicamba to yield phenols is a common route for microbial degradation of methoxylated aromatic compounds (Alexander, 1994. *Biodegradation and Bioremediation*. Academic Press, p. 46), such a Dicamba-specific demethylase should be present in microorganisms that have adapted to degrade Dicamba and it should be possible to isolate the methylase from these microorganisms.

2. 2-(2,4-dichlorophenoxy)-propionic acid (2,4-DP) or its amine or ester derivatives. Apparently, no pure cultures are available for degradation of this compound, but an enzyme similar to 2,4-D α-ketoglutarate dioxygenase, and specific to 2,4-DP, should be present in bacteria that have adapted in the presence of 2,4-DP and it should be possible to isolate such an enzyme from these bacteria.

3. 2-(4-chloro-2-methylphenoxy)-propionic acid (MCPP) and its amine, ester, and other derivatives. An enzyme similar to 2,4-D α-ketoglutarate dioxygenase, but specific for MCPP, would be employed to assay MCPP or, after hydrolysis, MCPP amine or ester derivatives. Such an enzyme should be found in and isolateable from bacteria that have adapted in the presence of MCPP or its derivatives. Several bacteria that degrade MCPP have been described (Lappin et al., *Appl. Environ. Microbiol.* 1985, 49, 429–433). These include "pseudomonads" (gram negative, respiratory bacteria), Alcaligenes, Pseudomonas, Actnetobacter, and Flavobacterium strains. This laboratory has reported the isolation of a pure culture of Alcaligenes that degrades one isomer of a racemic MCPP mixture and presented evidence that this strain employed a pathway similar to that used by other bacteria to degrade 2,4-D, i.e., formation of 4-chloro-2-methylphenol by cleavage of the phenoxy ether bond of MCPP, analogous to formation of 2,4-dichlorophenol from 2,4-D by dioxygenase cleavage of the phenoxy ether (V. Tett et al., Abstracts of the General Meeting, American Society for Microbiology, 1994, Abstract number Q-85: Biochemistry of mecoprop degradation by *Alcaligenese denitrificans*). Thus, a MCPP-specific enzyme for use in a MCPP assay should be present in such microorganisms.

4. (2,4,5,-trichlorophenoxy)acetic acid (2,4,5-T). An enzyme probably related to DDO cleaves 2,4,5-T to form 2,4,5-trichlorophenol (Karns et al., *Appl. Environm. Microbiol.* 1983, 46, 1182). The 2,4,5-T enzyme appears to attack 2,4-D, and thus might be substituted for DDO in a method for detection of 2,4-D; however, DDO does not cleave 2,4,5-T.

5. Many other compounds that contain ethers linked to an aromatic ring, including a variety of pesticides and herbicides. Examples of these are shown in FIG. 1, and include: 2,3-dihydro-2,2-dimethyl-7-benzofuranyl methylcarbamate (Carbofuran, Furadan®); p-chlorophenyl benzenesulfonate (Fenson); p-chlorophenyl p-clorobenzenesulfonate (Ovex, Ovotran®); 2-(p-tertbutylphenoxy)cyclohexyl 2-propynyl sulfite (Propargite, Omite®); 1-naphtyl methylcarbamate (Carbaryl, Sevin®); o,o-dimethyl o-2,4,5-trichlorophenyl methylphosphorothioate (Ronnel, Korian®); 4-tert-butyl-2-chlorophenyl methyl-methylphosphoroamidate (Crufomate, Ruelene®); o,o-dimethyl o-2-chloro-1-(2,4,5-trichlorophenyl) vinyl phosphate (Tetrachlorvinphos, Gardona®, Rabon®); o-(4-bromo-2-chlorophenyl)-o-ethyl-S-propyl phosphorothioate (Profenofos, Curacron®); o-ethyl S-propyl o-(4-methylthio) phenyl phosphorodithioate (Sulprofos, Bolstar®); 1-methylethyl 2-([ethoxy (1-methyl-ethyl) amino phosphinothioyl] oxy)benzoate (Isofenphos, Amaze®, Pryfon®); o,o-diethyl O-(2-isopropyl-4-methyl-6-pyrimidinyl) phosphorothioate (Diazinon); o,o-diethyl o-(3,5,6-trichloro-2-pyridyl) phosphorothioate (Chlorpyrifos, Dursban®, Lorsban®); 1,1,1-trichloro-2,2-bis(p-methoxyphenyl)ethane (Methoxychlor); butyl 2-(4-(5-trifluoromethyl-2-pyridyloxy)phenoxy) propionate (Fluazifop-butyl, Fusilade®); (±)-2-[4-[(6-chloro-2-benzoxazolyl)oxy]phenoxy]propanoic acid (Fenoxapropethyl, Whip®); 2-(4-(2,4-dichlorophenoxyphenoxy)-methyl-propanoate (Diclofop methyl, Hoelon®); (±)-2-[4-(6-chloro-2-quinoxalinyloxy)phenoxy]propanoic acid (Quizalofop-ethyl, Assure®); 4-dimethylamino-3,5-zylyl N-methylcarbamate (Mexacarbate, Zectran®); 2-sec-butyl-4,6-dinitrophenyl 3-methyl-2-butenoate (Binapacryl, Morocide®); 2-(1-methylheptyl)-4,6-dinitrophenyl crotonate (Dinocap, Karatbane®); 1-naphthyl N-methylcarbamate (Carbaryl, Sevin®); [(3,5,6-trichloro-2-pyridinyl)oxy]acetic acid (Triclopyr, Garlon®); [3-dimethylamino-(methylene-iminophenyl)]-N-methylcarbamate hydrochloride (Formetanate, Carzol®); 4-(methylthio)3,5-xylyl methylcarbamate (Methiocarb, Mesurol®); 4-(dimethylamino)-3-methylphenol methylcarbamate (Aminocarb, Matacil®); 2-(α-naphthoxy)-N,N-diethylpropionamide (Napropamide, Devrinol®); o-isopropoxyphenyl methylcarbamate (Propoxur, Baygon®); 2,2-dimethyl-1,3-benzo dioxol-4-yl methylcarbamate (Bendiocarb, Ficam®, Turcam®); 2-(2,4,5-trichlorophenoxy)propionic acid (Silvex); [(4-chloro-o-tolyl)oxy]acetic acid (MCPA); Chloroneb; [(4-amino-3,5-dichloro-6-fluoro-2-pyridinyl)oxy] acetic acid (Fluroxypyr, Starane®); and (±)-2-[4-[[3-chloro-5-(trifluoromethyl)-2-pyridinyl]oxy] phenoxy]propanoic acid (Haloxyfop-methyl, Verdict®, Gallant®). Enzymes which specifically cleave those compounds shown in FIG. 1 that are not cleaved by DDO may be isolated and cloned from organisms known to degrade these compounds.

Means for detecting phenolic products of the enzymatic cleavage of 2,4-D and related compounds.

The detection methods of the present invention preferably employ a color reaction for detecting phenolic compounds using 4-aminoantipyrine as a coupling reagent (E. Emerson, *J. Org. Chem.* 1943, 8, 417–419). Color changes in solutions with approximately 2 mg/l of a phenol can easily be seen by the unaided eye. Other sensitive assays for such phenolic compounds as are known in the art may also be used.

As discussed above, DDO cleaves the phenoxy ether bond of 2,4-D to form DCP. The red color resulting from a 2 mg/l of DCP solution is capable of being visually distinguished from a 2,4-D-free control (bright yellow) without using any analytical equipment.

Physical embodiments

Any of the physical embodiments of enzymatic assays known in the art may be employed in the practice of the present invention. For convenience of use in the field the enzyme employed to convert the 2,4-D or other phenoxy ether compound to a phenolic product is immobilized on a solid support (solid-phase matrix) either covalently or non-covalently by any of the means well known in the art.

Depending on the type of support and on the desired conditions, the solid support can be used in a number of different forms. For example, cells or cell-free lysates can simply be applied to and air dried on cellulose, e.g., filter bags, as described in Example 6. Other commonly used solid supports include, but are not limited to:

Nitrocellulose, commercially available as membranes or microtiter wells, with a protein capacity of 100 µg/cm$^2$. Binding to nitrocellulose is noncovalent.

Polyvinylchloride, commercially available as microtiter plates or sheets, with a protein capacity of 300 ng/cm$^2$. Binding is noncovalent.

Polystyrene, commercially available as beads and microtiter plates, with a protein capacity of 300 ng/cm$^2$. Binding is noncovalent.

Diazotized paper, commercially available as sheets, with a protein capacity of greater than 10 mg/cm$^2$. Binding is covalent, through free amino groups.

Activated beads, with a protein capacity of approximately 10 mg/ml. Binding is covalent. Bead matrices include, but are not limited to, agarose, cross-linked agarose, copolymers of agarose and polyacrylamide, and polyacrylic. Activators providing binding groups include carbonyldiimidozole, cyanogen bromide, glutaraldehyde, hydroxysuccinimide, tosyl chloride.

These and other solid supports, commercial examples, and discussions of their preparation and use are well known in the art and are discussed, e.g., in Harlow and Lane. *Antibodies: A Laboratory Manual.* Cold Spring Harbor Laboratory: Cold Spring Harbor, N.Y., 1988, pp. 528–537, 605–612.

Preferred solid supports for the practice of the present invention are test strips or "dipsticks," (see, e.g., DNA DipStick Kit™ (Invitrogen, San Diego, Calif., catalog no. K5632-01), beads, or (cellulose) "tea bags".

Definitions and Methods

The following definitions and methods are provided to better define the present invention and to guide those of ordinary skill in the art in the practice of the present invention.

Enzymes. Enzymes capable of cleaving the phenoxy ether bond of compounds such as 2,4-D to produce phenolic compounds detectable by the 4-aminoantipyrine colorimetric assay may be derived from bacterial sources, but may also be produced by fungi, plants, and animals. Such a enzymes may be isolated from a natural source, be chemically synthesized, or, preferably, be produced by the expression of a recombinant nucleic acid encoding the enzyme. Techniques for chemical synthesis of polypeptides are described, for example, in Merrifield, *J. Amer. Chem. Soc.*, 1963, 85, 2149–2156.

The preferred enzyme for the methods and compositions of the present invention is a 2,4-D α-ketoglutarate dioxygenase, including the 2,4-D α-ketoglutarate dioxygenase of *Alcaligenes eutrophus* JMP134 (the product of the tfdA gene) and enzymes having an amino acid sequence substantially homologous to that of the naturally occurring 2,4-D α-ketoglutarate dioxygenase polypeptide. The present invention encompasses the use only of those enzymes that retain the ability, after drying and rehydration, to cleave the phenoxy ether bond of a target compound to form a phenolic product, e.g., to convert 2,4-D to 2,4-dichlorophenol. Those of skill in the art will be able to easily assay such variants for the required activity by the 4-aminoantipyrine method described herein or another method well known in the art.

An enzyme that is "substantially homologous" to the native 2,4-D α-ketoglutarate dioxygenase polypeptide has an amino acid sequence at least about 50%–70% homologous. More preferably, the homology is at least 70%–90%. Thus, enzymes useful in the practice of the present invention include enzymes having minor variations in the polypeptide sequence of the naturally occurring 2,4-D α-ketoglutarate dioxygenase polypeptide, including minor substitutions, deletions, insertions or other modifications of the native polypeptide.

Amino acid substitutions are typically of single residues; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Those of skill in the are will readily appreciate that conservative amino acid substitutions generally have no effect or only a small effect on biochemical characteristics (e.g., enzyme activity, binding of substrates, etc.) of an enzyme. Table 1 shows amino acids which may be substituted for an original amino acid in a protein and which are regarded as conservative substitutions.

TABLE 1

Conservative Amino Acid Substitutions

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial enzyme variants include enzymes with amino acid substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The present invention also embraces naturally occurring enzymes (and their substantial homologs) other than 2,4-D α-ketoglutarate dioxygenase that, like 2,4-D α-ketoglutarate dioxygenase, are capable of cleaving the phenoxy ether bond of a target compound to produce a phenolic product and that retains activity upon drying and rehydration.

Based upon the nucleotide sequence of the tfdA gene of *Alcaligenes eutrophus* JMP134, probes and/or primers may readily be designed in order to obtain from other bacterial strains or species nucleic acids encoding DDOs and having a sequence that is substantially similar to that of the 2,4-D α-ketoglutarate dioxygenase of *Alcaligenes eutrophus* JMP134.

Alternatively, for useful enzymes encoded by nucleic acids lacking sufficient homology with the tfdA gene to be cloned using probes and primers based on the tfdA sequence, it will be necessary to purify the enzyme from an organism known to be able to degrade the target compound and to clone the gene encoding the enzyme. The gene may be cloned by generating antibodies specific for the enzyme for use in probing a cDNA library constructed in an expression vector such as bacteriophage λgt11. Alternatively, the amino acid sequence of the purified enzyme may be determined and used to produce degenerate nucleic acid probes to screen cDNA or genomic libraries. Any of a variety of methods well known in the art for constructing and screening cDNA and genomic DNA libraries may be employed, as described, e.g., in Sambrook et al., 1989, and Ausubel et al., 1987.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

Enzyme purification. Enzymes useful in the practice of the present invention may be in either a purified, partially purified, or impure state. An enzyme polypeptide is "purified" if it has been separated from the cellular components (nucleic acids, lipids, carbohydrates, and other polypeptides) that naturally accompany it.

The enzymes of the present invention may be purified by any of the various means known in the art. Various methods of protein purification are described, e.g., in *Guide to Protein Purification*, M. Deutscher, ed., *Methods in Enzymology*, vol. 182 (Academic Press: San Diego, 1990) and R. Scopes, *Protein Purification: Principles and Practice* (Springer Verlag: New York, 1982).

Nucleic acids. Enzymes useful for the practice of the present invention, as defined above, may be produced by the expression in an appropriate host cell of a recombinant nucleic acid (DNA or RNA) that encodes the enzyme. Such nucleic acids include the naturally occurring (i.e., "native" or "wild type") nucleic acids encoding the enzyme, e.g., the tfdA gene of *Alcaligenes eutrophus* JMP134. Also included are nucleic acids that (1) are "substantially similar" (as defined below) to such naturally occurring nucleic acids and (2) encode a naturally occurring enzyme useful in the practice of the present invention or a substantial homolog thereof, as defined above.

A first nucleic acid is "substantially similar" to a second nucleic acid if, when optimally aligned (with appropriate nucleotide insertions or deletions) with the other nucleic acid (or its complementary strand), there is nucleotide sequence identity in at least about 75% of the nucleotide bases.

Alternatively, substantial similarity exists when a first nucleic acid hybridizes to a second nucleic acid (or a complementary strand thereof) under stringent hybridization conditions. Stringent hybridization conditions are functionally defined by the hybridization procedure discussed in Sambrook et al., *Molecular Cloning: A Laboratory Manual*, 2nd ed., vol. 1–3, Cold Spring Harbor Laboratory Press: Cold Spring Harbor, N.Y., 1989 at 9.52–9.55. See also, Sambrook et al., 1989 at 9.47–9.52, 9.56–9.58; Kanehisa, *Nuc. Acids Res.*, 1984, 12, 203–213; Wetmur and Davidson, *J. Mol. Biol.*, 1968, 31, 349–370. Nucleic acid hybridization is affected by such conditions as salt concentration, temperature, or organic solvents, in addition to the base composition, length of the complementary strands, and the number of nucleotide base mismatches between the hybridizing nucleic acids, as will be readily appreciated by those skilled in the art.

Techniques for nucleic acid manipulation are described generally in, for example, Sambrook et al., *Molecular Cloning: A Laboratory Manual*, 2nd ed., vol. 1–3, Cold Spring Harbor Laboratory Press: Cold Spring Harbor, N.Y., 1989; and F. Ausubel et al., *Current Protocols in Molecular Biology*, Greene Publishing and Wiley-Interscience: New York, 1987 (with periodic updates). Reagents for the practice of such techniques are known in the art and are widely available from commercial vendors.

"Encode". A nucleic acid is said to "encode" a polypeptide if the nucleic acid can be transcribed and/or translated to produce the polypeptide, whether in its native state or after manipulation by methods well known in the art. The anti-sense strand of such a nucleic acid is also said to encode the sequence.

"Operably Linked". A first nucleic acid sequence is operably linked with a second nucleic acid sequence when the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is one that has a sequence that is not naturally occurring, or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. For example, a recombinant nucleic acid can be produced in order to replace a codon with a different codon encoding the same or a conservative amino acid or to join together nucleic acid segments to generate a new combination of functions.

Preparation of recombinant or chemically Synthesized nucleic acids; vectors, transformation, host cells. Large amounts of the enzymes useful in the practice of the present invention may be produced by expression in a suitable host cell of a recombinant nucleic acid encoding the enzyme.

To that end, natural or synthetic DNA fragments coding for the enzyme are incorporated into recombinant nucleic acid constructs, typically DNA constructs, capable of introduction into and replication in a host cell. Usually the DNA constructs will be suitable for replication in a unicellular host, such bacteria, but may also be intended for introduction into yeast, mammalian, plant or other eukaryotic cells.

Expression vectors are DNA constructs prepared for introduction into a prokaryotic or eukaryotic host typically comprising a replication system recognized by the host, including the intended DNA fragment encoding the desired polypeptide, and will preferably also include transcription and translational initiation regulatory sequences operably linked to the polypeptide encoding segment. Expression vectors may include, as required, an origin of replication or autonomously replicating sequence (ARS) and expression control sequences, a promoter, an enhancer and any necessary processing information sites, including ribosome-binding sites, RNA splice sites, polyadenylation sites, transcriptional terminator sequences, and mRNA stabilizing sequences, and selectable markers (e.g., genes encoding resistance to antibiotics or other toxic substances, complementing auxotrophic deficiencies, or supplying critical nutrients not available from complex media). Secretion signals may also be included. For appropriate enhancer and other expression control sequences see also, *Enhancers and Eukaryotic Gene Expression*, Cold Spring Harbor Press: Cold Spring Harbor, N.Y., 1983. In addition, the construct may be joined to an amplifiable gene (e.g., DHFR) so that multiple copies of the gene may be made. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3- phosphate dehydrogenase, enzymes responsible for maltose and galactose utilization, and others. Suitable vectors and promoters for use in yeast expression are further described in Hitzeman et al. EP 73,657A. Appropriate non-native mammalian promoters might include the early and late promoters from SV40 (Fiers et al., *Nature* 1978, 273, 113) or promoters derived from murine Moloney leukemia virus, mouse mammary tumor virus, arian sarcoma viruses, adenovirus II, bovine papilloma virus or polyoma.

Expression vectors may be prepared by means of standard recombinant techniques well known in the art and discussed, for example, in Sambrook et al., 1989, or Ausubel et al., 1987. The expression vector may be introduced into a host cell by any of the various means known in the art, which vary depending on the type of cellular host, and include: electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989, and Ausubel et al., 1987. While suitable expression vectors will preferably replicate autonomously, they may also be inserted into the genome of the host cell by means well known in the art.

Examples of functional combinations of cell lines and expression vectors are described in the Examples below and in Sambrook et al., 1989, or Ausubel et al., 1987; see also, e.g., Metzger et al., *Nature*. 1988, 334, 31–36. Appropriate prokaryotic hosts include strains of *Escherichia coli* and *Pseudomonas aeruginosa*, although other prokaryotes known in the art may also be used. Mammalian or other eukaryotic host cells, such as those of yeast, filamentous fungi, plant, insect, amphibian or avian species, may also be useful for production of the proteins of the present invention. See, *Tissue Culture*, Kruse and Patterson, ed., Academic Press, 1973. Examples of commonly used mammalian host cell lines are VERO and HeLa cells, Chinese hamster ovary (CHO) cells, and WI38, BHK, and COS cell lines, or others which may be appropriate, e.g., to provide higher expression, desirable glycosylation patterns, or other features.

The invention will be better understood by reference to the following examples, which are intended to merely illustrate the best mode now known for practicing the invention. The scope of the invention is not to be considered limited thereto, however.

EXAMPLES

Example 1

2,4-Dichlorophenoxyacetic Acid (2,4-D). Detection using 2,4-D α-Ketoglutarate Dioxygenase The best understood degradation pathway of 2,4-D is encoded on plasmid pJP4 from *Alcaligenes eutrophus* JMP134 (R. Don and J. Pemberton, *J. Bacteriol.* 1981, 145, 681–686; R. Don et al., *J. Bacteriol.* 1985, 161, 85–90; R. Don and J. Pemberton, *J. Bacteriol.* 1985, 161, 466–468). The first step in the pathway involves the conversion of 2,4-D into DCP (R. Don et al., *J. Bacteriol.* 1985, 161, 85–90). Originally, this reaction was thought to be carried out by a monooxygenase, but it was later found to be catalyzed by an α-ketoglutarate-dependent dioxygenase (F. Fukumori and R. Hausinger, *J. Bacteriol.* 1993, 175, 2083–2086). The gene for this enzyme was designated as tfdA. The expression of tfdA is regulated by 2,4-D. Further in the pathway, DCP is converted into 3,5-dichlorocathechol (DCCAT) by 2,4-D hydroxylase, which is also encoded on pJP4 by gene tfdB (R. Don et al., *J. Bacteriol.* 1985, 161, 85–90; T. Liu and P. Chapman, *FEBS Letters* 1984, 173, 314–318). Thus, no DCP accumulates in media when cultivating microorganisms containing pJP4. Cleavage of DCCAT by a dioxygenase yields 2,4-dichloromuconic acid. A lactonizing enzyme then forms cis-2-chlorodiene lactone and chloromaleylacetic acid is finally produced by a lactonase (R. Don et al., *J. Bacteriol.* 1985, 161, 85–90; B. Kaphmmer and R. Olsen, *J. Bacteriol.* 1990, 172, 5856–5862.).

The genes encoding these enzymes, tfdA, tfdB and tfdCDEF, have been located on plasmid pJP4 (B. Kaphmmer and R. Olsen, *J. Bacteriol.* 1990, 172, 5856–5862; B. Kaphmmer et al., *J. Bacteriol.* 1990, 172, 2280–2286; E. Perkins and P. Lurquin, *J. Bacteriol.* 1988, 170, 5669–5672; W. Streber et al., *J. Bacteriol.* 1987, 169, 2950–2955). The expression of tfdB is regulated by the product of gene tfdS using 2,4-D and DCP as effectors (B. Kaphmmer and R. Olsen, *J. Bacteriol.* 1990, 172, 5856–5862). Since both 2,4-D and DCP can induce the expression of tfdB, DCP is further transformed by microorganisms bearing pJP4 or its derivatives, pRO101 or pRO103 (A. Harker et al., *J. Bacteriol.* 1989, 171, 314–320). No DCP can be detected by the color reaction in the culture media of these microorganisms when 2,4-D is supplied.

Plasmid pRO103 is a derivative of pJP4 obtained by insertion of Tn1721 into a nonessential region of pJP4 DNA and deletion of a 3.9 kilobase (kb) fragment from pJP4 (A. Harker et al., *J. Bacteriol.* 1989, 171, 314–320; B. Kaphmmer et al., *J. Bacteriol.* 1990, 172, 2280–2286). Tn1721 contains the gene for tetracycline resistance. The 3.9 kb deleted fragment of pJP4 contains a negative control-regulatory gene (tfdR), which regulates the expression of tfdA by the inducer 2,4-D. Thus, gene tfdA in pRO103 is constitutively expressed (A. Harker et al., *J. Bacteriol.* 1989, 171, 314–320). Strains carrying plasmid pRO103 have elevated basal levels of 2,4-D α-ketoglutarate dioxygenase; since the tfdA gene is expressed constitutively, it cannot be "turned off" (B. Kaphmmer and R. Olsen, *J. Bacteriol.* 1990, 172, 5856–5862). While no DCP was accumulated in *Pseudomonas aeruginosa* PAO1 (pRO103), we found that the cell-free extract of *P. aeruginosa* PAOpb 1pk (pRO103) converted 2,4-D into DCP, which accumulated.

A recombinant microorganism, *E. coli* DH5α (pYG3), was constructed for the production of 2,4-D α-ketoglutarate dioxygenase (DDO) for 2,4-D detection (Example 1). A 1.4 kb XbaI-SalI fragment of pRO101, which contains gene tfdA, was cloned into the plasmid vector pBluescript® SIC (Stratagene, Inc., La Jolla, Calif.), an expression vector, with the promoter lacZ. The constructed plasmid was designated as pYG3. Gene tfdA in pYG3 was inducible by isopropyl β-D-thiogalactopyranoside (IPTG) and was expressed at a high level.

The cell-free extract of *E. coli* DH5α (pYG3) was directly used for 2,4-D detection, and enzyme purification was not necessary. The cell-free extract proteins were dried in a filter paper bag, which was used as an enzyme delivery method in 2,4-D detection. This 2,4-D detection system detected 2,4-D concentration at 2 mg/l within 10 minutes, and was stable for at least 3 months when stored at room temperature.

Cloning of tfdA. *E. coli* (pRO101), a gift from Dr. R. H. Olsen at the University of Michigan, was used to obtain a DNA fragment containing the gene tfdA. Plasmid pRO101 is a derivative of plasmid pJP4 containing Tn1721 inserted into a nonessential region (A. Harker et al., *J. Bacteriol.* 1989, 171, 314–320).

LB medium was used for all cultures. 50 mg/l of tetracycline was supplied to select for the culture of E. coli (pRO101). 75 mg/l of ampicillin was supplied for all other cultures.

The cultures for plasmid preparations were grown in 5 ml of media in an orbital incubator-shaker at 37° C. and 200 rpm. The cultures for enzyme production were grown in an incubator-shaker at 200 rpm at 30° C. with 500 ml media inoculated with a 5 ml culture grown overnight at 37° C.

The construction of pYG3 from pBluescript® SK⁺ and a 1.4 kb SalI-XbaI fragment of pRO101 is schematically shown in FIG. 2. There are more than ten SalI restriction sites and at least two XbaI restriction sites on pRO101. Although the restriction map of pRO101 by SalI and XbaI is unpublished, the nucleotide sequence of a 2.06 kb BamHI-SalI fragment of pJP4 encoding the DDO gene tfdA has been published (E. Perkins and P. Lurquin, *J. Bacteriol.* 1988, 170, 5669–5672). There is an XbaI site at 110 bp before the tfdA start codon and a SalI site 440 bp after the tfdA stop codon. Also, there is an EcoRI site within tfdA. Based on the restriction map of pBluescript® SK⁺ (Stratagene Product Catalog, 1994) and the sequence of the SalI-XbaI fragment, the restriction map of pYG3 was determined, as shown in FIG. 2.

Plasmid pRO101 was isolated from *E. coli* (pRO101) by the procedure of Hansen and Olsen (J. Hansen and R. Olsen, *J. Bacteriol.* 1978, 135, 227–238). 50 ml cell culture was used in each isolation. The DNA sample was further purified by: (1) incubation with 10 mg/l RNase for 15 minutes; (2) phenol extraction; and (3) ethanol precipitation (twice) (F. Ausubel, 1992. *Short Protocols in Molecular Biology*. 2nd ed. John Wiley & Sons, New York).

Wizard™ Minipreps DNA Purification System (Promega, Madison, Wis.) was used to isolate plasmid pBluescript® SK⁺ and pYG3 from 3 ml overnight cultures according to manufacturer instructions.

The DNA fragment containing gene tfdA, which is about 1.4 kb, was obtained by digesting pRO101 with XbaI and SalI restriction endonucleases sequentially at 37° C. The pRO101 DNA sample was first digested by XbaI in Medium Salt Buffer (USB, Cleveland, Ohio) for 2 hours. Then the salt concentration was adjusted to 120 mM and the DNA was further digested by SalI for an additional 2 hours. The digested sample was separated by 1.5% agarose gel electrophoresis. DNA fragment sizes were determined using the 1 kb DNA Ladder and High Molecular Weight DNA Markers (GIBCO BRL, Gaithersburg, Md.). The 1.4 kb fragment containing tfdA was cut out from the gel, and then purified by a QIAEX (QIAGEN) DNA purification kit (Quigen, Inc., Chatsworth, Calif.).

The vector used for tfdA expression was pBluescript® SK⁺, which was also maintained and produced in *E. coli* DH5α. The vector was also digested by XbaI and by SalI, and purified by agarose gel separation and QIAEX.

Ligation was performed using T4 DNA ligase (0.3 units) in a 10 μl volume at 16° C. for 11 hours according to standard methods (Sambrook et al., 1989). All enzymes used for cloning were provided by USB.

The ligation solution was diluted 5-fold before transformation. Diluted ligation solution (5 μl) was used for the transformation of 100 μl of competent *E. coli* DH5α by standard methods (Sambrook et al., 1989). Transformants were selected and screened on LB plates with ampicillin (75 mg/l), 5-bromo-4-chloro-3-indolyl-β-D-galactoside (X-gal) and isopropyl β-D-thiogalactopyranoside (IPTG).

The hybrid plasmid constructed from pBluescript® SK⁺ and the DNA fragment containing gene tfdA was designated pYG3. *E. coli* DH5α [φ80dkacZΔM15, Δ(lacZYA-argF), U169, deoR, recA1, endA1, hsdR17, supE44, thi-1, gyrA96, relA1] was used as the host cell for the expression of gene tfdA from pYG3. The recombinant organism, *E. coli* DH5α (pYG3), was maintained on LB agar plates with 75 mg/l ampicillin and stored at 4° C.

Figure 3:
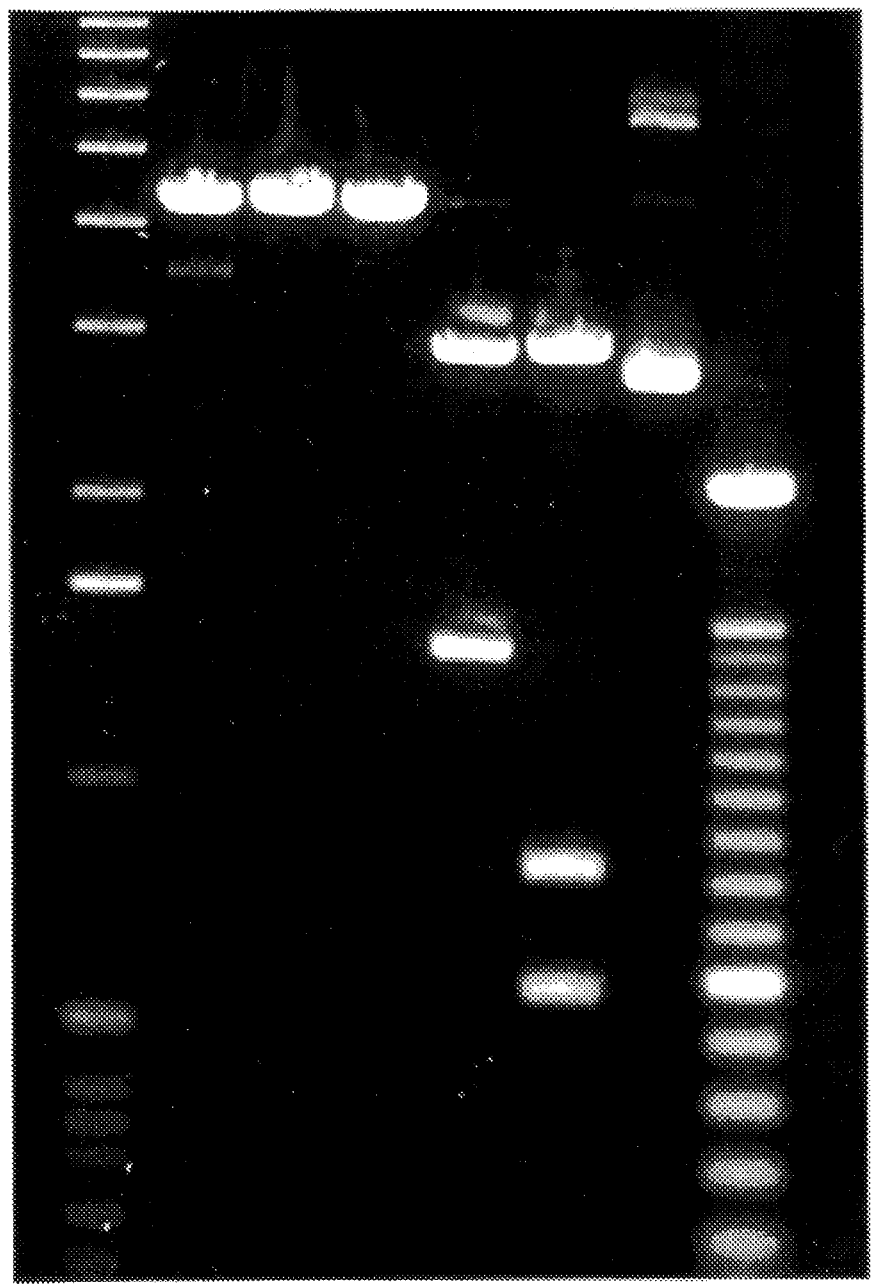
FIG. 3 shows a restriction site analysis of pYG3. Lane 1, 1 kilobase (kb) Ladder; lane 2, SalI; lane 3, XbaI; lane 4, EcoRI; lane 5, XbaI and SalI; lane 6, XbaI, SalI and EcoRI; lane 7, undigested; lane 8, 100 base pair (bp) ladder.

A restriction site analysis for pYG3 is shown in FIG. 3. DNA for pYG3 was digested with the restriction enzymes indicated and the fragments separated by agarose gel electrophoresis. There was only one restriction of XbaI, SalI and EcoRI in pYG3. The size of pYG3 was 4.36 kb from the gel (Lane 2, 3 & 4). The size of inserted DNA fragments was 1.43 kb, and the size of pBluescript® was 2.93 kb (Lane 5). The inserted DNA fragments could be cut by EcoRI into 0.84 kb and 0.57 kb fragments (Lane 6). The size of fragments in FIG. 3 matched the size calculated from published data (FIG. 2), indicating that the correct DNA fragment was cloned.

Example 2

Expression of tfdA in *E. coli*

The promoter of gene tfdA is located in the vicinity of the XbaI site of pYG3, which is 110 bases before the tfdA start codon (E. Perkins and P. Lurquin, *J. Bacteriol.* 1988, 170, 5669–5672). Cloning of this 1.4 kb fragment placed tfdA under the control of the lacZ promoter. *E. coli* DH5α was used as the host cell for the expression of tfdA on pYG3. While tfdA was not expressed in the medium with glucose alone, it was expressed in LB medium when IPTG was added as an inducer.

*E. coli* DH5α (pYG3) cultures (500 ml) were grown in 1 liter flasks. When $ID_{560}$ reached approximately 2.5, 200 μl of 115 mg/ml IPTG (46 μg/l final concentration) were added to induce the expression of gene tfdA. One hour after adding IPTG, cells were harvested by centrifugation (8,000×g) for 10 minutes at 4° C., washed with 25 ml of 100 mM sodium phosphate buffer (pH 8.0), then resuspended in 25 ml of the phosphate buffer. Cell-free extracts were obtained bypassing the cells once through a pre-chilled French press at 1500 psi then clarifying the debris by centrifugation (16,000×g) for 20 minutes at 4° C.

Protein concentrations were determined as described by Bradford (*Anal. Biochem.* 1976, 72, 248–254), using dye reagents supplied by Bio-Rad (Richmond, Calif.). Bovine serum albumin (BSA) was used as a standard for calibration.

The enzyme activities of cell-free extracts were determined from DCP concentration measurements after incubation at room temperature (20° C.) in 125 mg/l 2,4-D and 10 mM sodium phosphate buffer (pH 8.0) containing 100 μM ferrous ammonium sulfate and 1 mM α-ketoglutarate. DCP concentration was determined by the 4-aminoantipyrine method (P. Amy et al., *Appl. Environ. Microbiol.* 1985, 49, 1237–1245). The assay was similar to the one used by Fukumori and Hausinger (F. Fukumori and R. Hausinger, *J. Bacteriol.* 1993, 175, 2083–2086).

Example 3

Optimization of Fermentation Conditions for Production of 2,4-D α-Ketoglutarate Dioxygenase by Recombinant *Pseudomonas aeruginosa* pAO1 (pRO103)

Kinetic studies of the production of recombinant DDO in *P. aeruginosa* PAO1 (pRO103) and *E. coli* DH5α (pYG3) (Example 3) were performed in order to optimize media and fermentation conditions for production of the enzyme. Also, the kinetics of cell growth and enzyme formation were determined.

Mathematical models. A general model describing microbial cell growth is (Kargi and Shuler, *Bioprocess Engineering: Basic Concepts*. Prentice Hall: Englewood Cliffs, Calif., 1992, p. 176):

$$\frac{dX}{dt} = \mu X \left(1 - \frac{X}{X_{max}}\right) \quad (1)$$

where X is the cell concentration, t is the time, $\mu$ is the specific growth rate, and $X_{max}$ is the maximum cell concentration.

The solution to equation 1 is the logistic equation:

$$X(t) = \frac{X_0 \exp(\mu t)}{1 - \frac{X_0}{X_{max}}[1 - \exp(\mu t)]} \quad (2)$$

where $X_0$ is the initial cell concentration.

A commonly used product formation model is the Leudeking and Piret model (R. Leudeking and E. Piret, *J. Biochem. Microbiol. Technol. Eng.* 1959, 1, 393–412):

$$\frac{dP}{dt} = m\frac{dX}{dt} + nX \quad (3)$$

in which P is the enzyme concentration, m and n are model parameters. Gene tfdA of pRO103 was constitutively expressed, and enzyme formation was growth related (n=0). According to the foregoing, enzyme formation by *P. aeruginosa* PAO1 (pRO103)-as a function of time can be expressed as:

$$P(t) = m \frac{X_0 \exp(\mu t)}{1 - \frac{X_0}{X_{max}}[1 - \exp(\mu t)]} \quad (4)$$

The following model can be used for enzyme formation by *E. coli* DH5α (pYG3), assuming enzyme production is not growth related (m=0):

$$P(t) = \int_{\Delta t}^{t} nX dt \quad (5)$$

in which $\Delta t$ is the time delay for enzyme expression.

Growth and maintenance of *P. aeruginosa* pAO1 (pRO103). Pseudomonas aeruginosa PAO1 (pRO103), a gift from Dr. R. H. Olsen of the University of Michigan, was stored at −20° C. in 50% glycerol solution. A minimal medium containing 6 g/l $Na_2HPO_4$, 3 g/l $KH_2PO_4$, 1 g/l $NH_4Cl$, 0.5 g/l NaCl and 3 mg/l $CaCl_2$ (pH 7.0) was used for cultivation of both *P. aeruginosa* and *E. coli*. Glucose was used as a carbon and energy source for *P. aeruginosa* PAO1 (pRO103), and 25 mg/l of mercury as $HgCl_2$ was supplied for selective pressure. Batch cultures of *P. aeruginosa* PAO1 (pRO103) were held in 300 ml flasks with 100 ml media for the optimization of media and operating condition. The flasks were shaken on a rotary shaker at 200 rpm and incubated at 30° C. Cell mass and enzyme activities were compared at late log phase. Cell mass was measured by a spectrophotometer (model 8542A, Hewlett-Packard, Palo Alto, Calif.) at 560 nm with a 1 cm path length.

Batch cultures of *P. aeruginosa* PAO1 (pRO103) were held in a 1000 ml fermenter (Microferm, New Brunswick Scientific Co., Edison, N.J.) containing a 350 ml working volume for modeling cell growth and enzyme production. The cultures were inoculated with overnight cultures from flasks. The agitation speed was 150 rpm and the aeration rate was 0.05 l/min. Foaming was controlled manually. The pH of the culture was not controlled.

Figure 4:
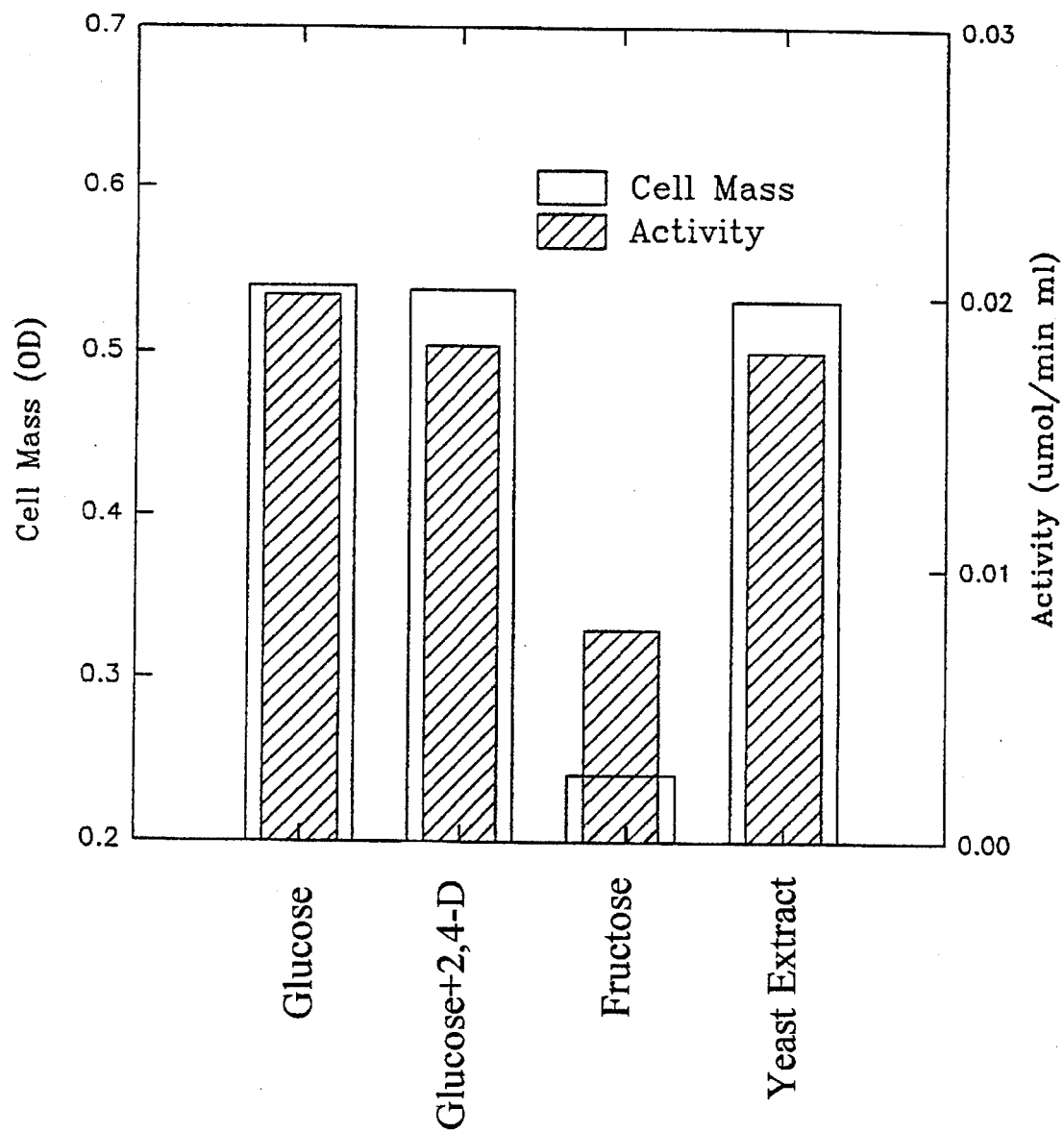
FIG. 4 plots the effects of carbon sources on cell growth and enzyme formation by P. aeruginosa PAO1 (pRO103).

Carbon sources. *P. aeruginosa* PAO1 (pRO103) could not grow on acetate, sucrose, or 2,4-D as sole carbon and energy sources, but could grow on glucose, yeast extract and fructose. The results of cell growth and enzyme formation with these carbon sources are shown in FIG. 4. Cell growth rates on glucose, glucose with 2,4-D, and yeast extract were nearly the same. As expected, 2,4-D was not essential for enzyme production, since gene tfdA of pRO103 was constitutively expressed. Furthermore, 2,4-D reduced enzyme production. Enzyme production on glucose was approximately 10% higher than on glucose with 2,4-D or yeast extract. Therefore, glucose was selected as the carbon source for further study with *P. aeruginosa* PAO1 (pRO103).

Figure 5:
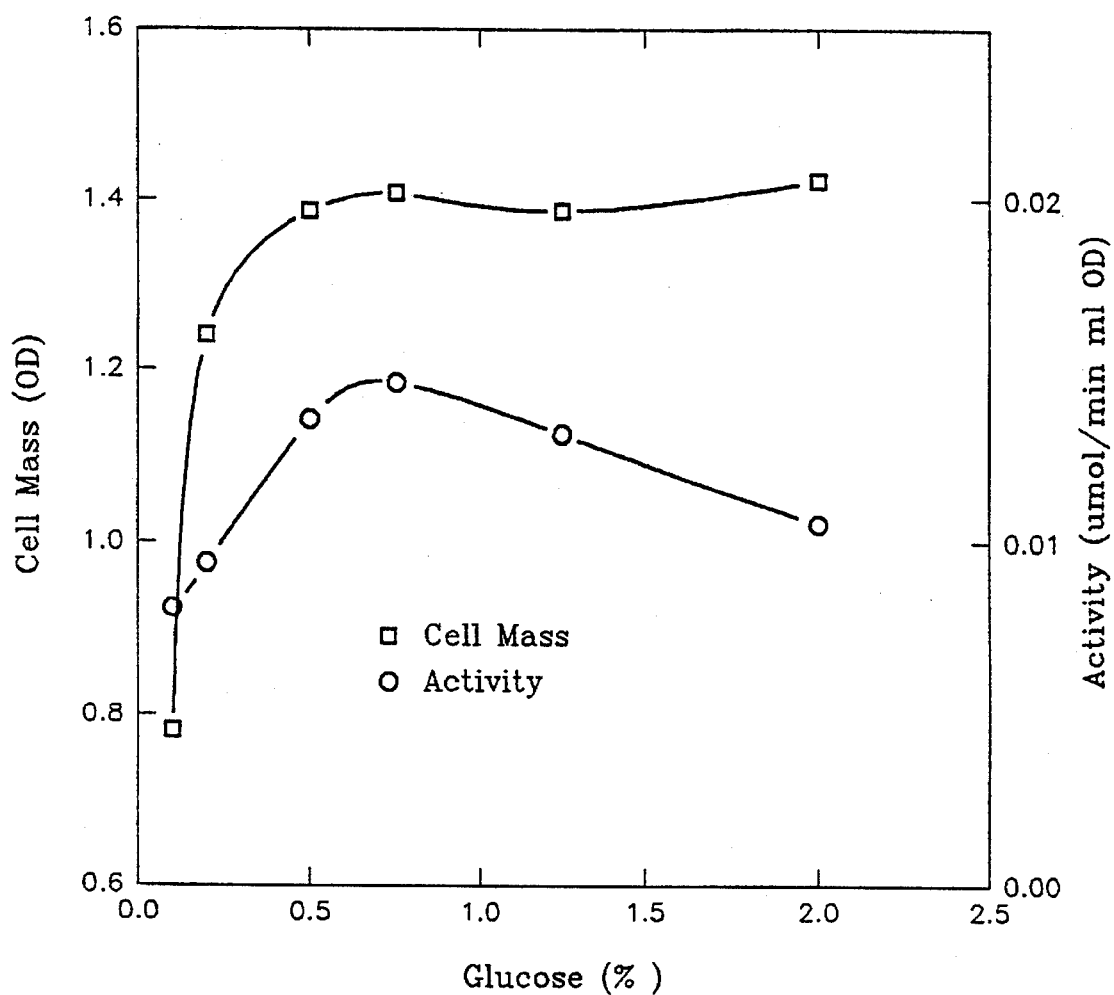
FIG. 5 plots the effects of glucose concentration on cell mass and enzyme activity by P. aeruginosa PAO1 (pRO103).

Glucose concentration. The effects of glucose concentration on cell growth and enzyme production are shown in FIG. 5. When glucose concentration was less than 0.5% wt./vol., glucose concentration had a strong effect on cell growth. Above a glucose concentration of 0.5%, cell concentration was not affected by glucose concentration. Glucose concentration affected enzyme production, not only through cell growth but also through the level of enzyme expression. As the glucose concentration increased, enzyme activity per unit of cell mass increased at glucose concentrations less than 0.75%, and decreased at glucose concentrations greater than 0.75%. Therefore, combining the effects of glucose concentration on cell growth and enzyme expression level, 0.75% was selected as the glucose concentration for maximum enzyme production.

Figure 6:
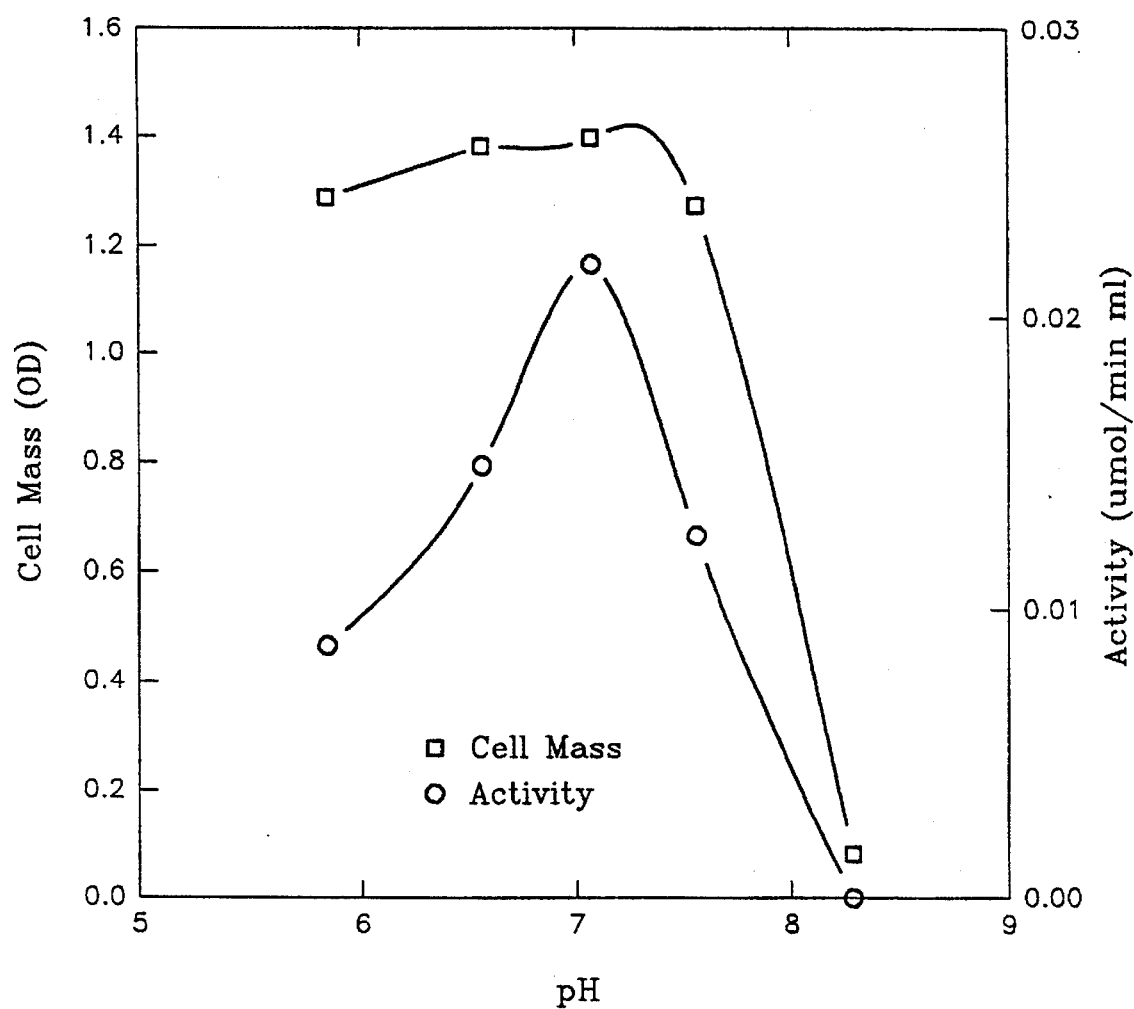
FIG. 6 plots the effects of pH on cell mass and enzyme activities by P. aeruginosa PAO1 (pRO103).

Medium pH. The effects of pH on cell growth and enzyme production are shown in FIG. 6. From pH 5.8 to 7.5, the effect of pH on cell growth was small. Growth was minimal at pH 8.5. In contrast to cell growth, enzyme productivity was strongly affected by pH in the range of pH 5.8 to 7.5. The optimum pH for enzyme production was 7.0. Enzyme activity in pH 6.5 and 7.5 media was approximately 30% lower than that at pH 7.0.

Figure 7:
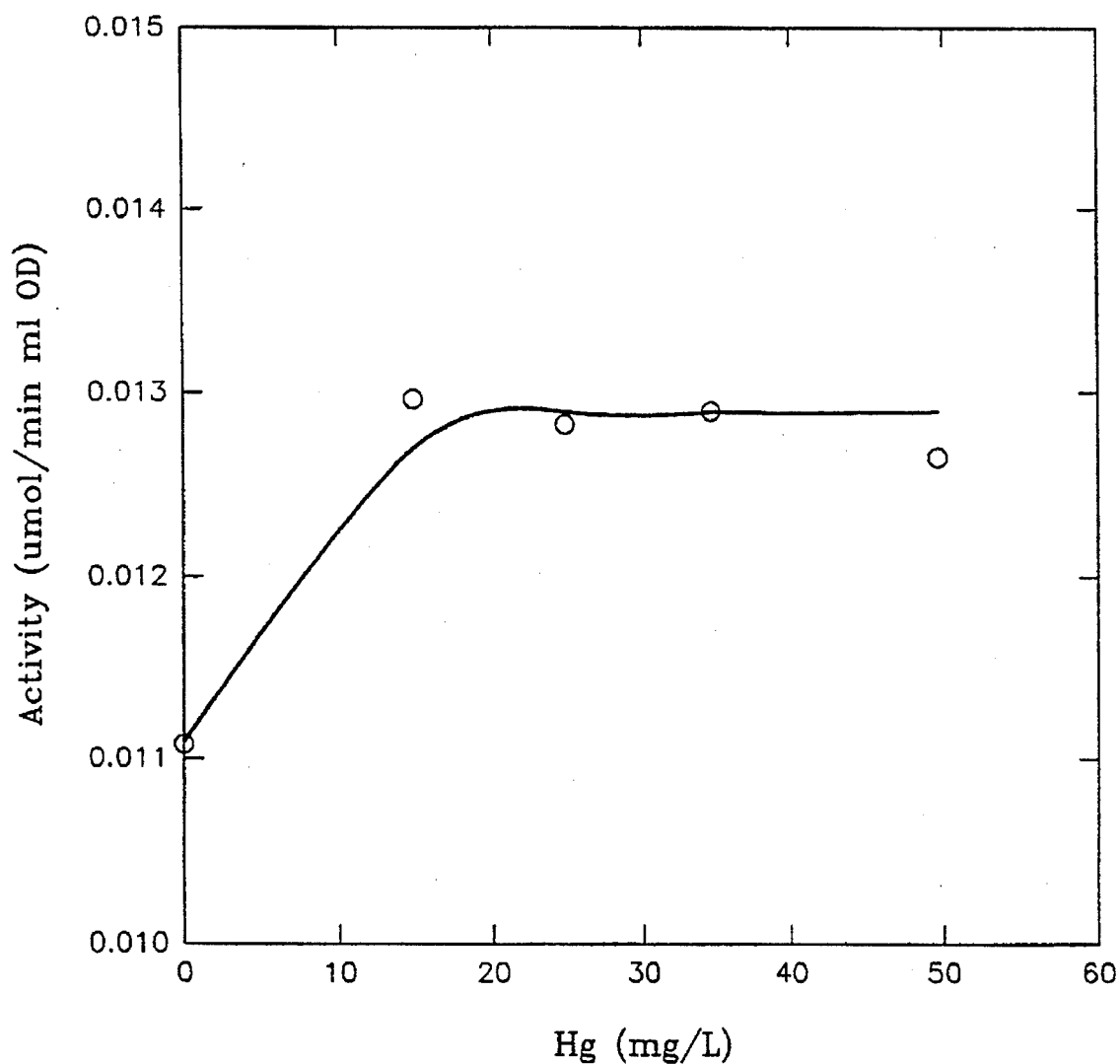
FIG. 7 plots the effects of mercury concentration on enzyme activity by P. aeruginosa PAO1 (pRO103).

Mercuric chloride concentration. Plasmid pRO103 has resistance genes to tetracycline and mercury. Mercuric chloride was used to select for cells containing pRO103 during cultivations. Measurements of enzyme productivity at different mercury concentrations are shown in FIG. 7. When mercury concentration was greater than 12.5 mg/l, mercury concentration did not affect enzyme production. However, without mercury in the media, the enzyme expression level was approximately 15% lower, although the cells remained tetracycline resistant.

Figure 8:
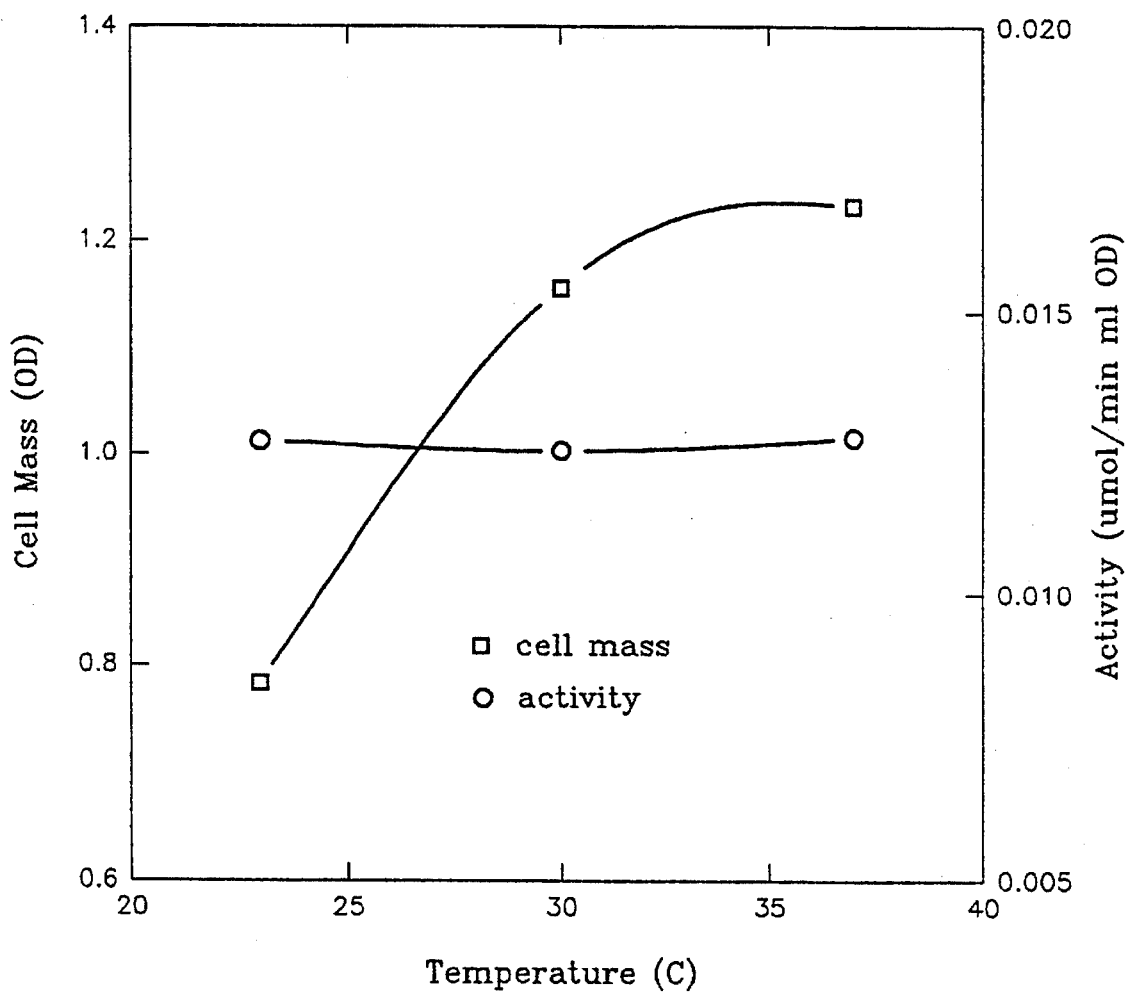
FIG. 8 plots the effects of temperature on cell mass and enzyme activity by P. aeruginosa PAO1 (pRO103).

Temperature. Three temperatures, 23° C., 30° C. and 37° C., were investigated. Cell growth was strongly affected by cultivation temperature, with the highest rate of growth at 37° C. (FIG. 8). However, enzyme activity per unit of cell mass was not affected by cultivation temperature. Therefore, to maximize enzyme productivity, a high temperature, 37° C., was preferred. The recommended enzyme production conditions for *P. aeruginosa* PAO1 (pRO103) are summarized in Table 2.

Figure 9:
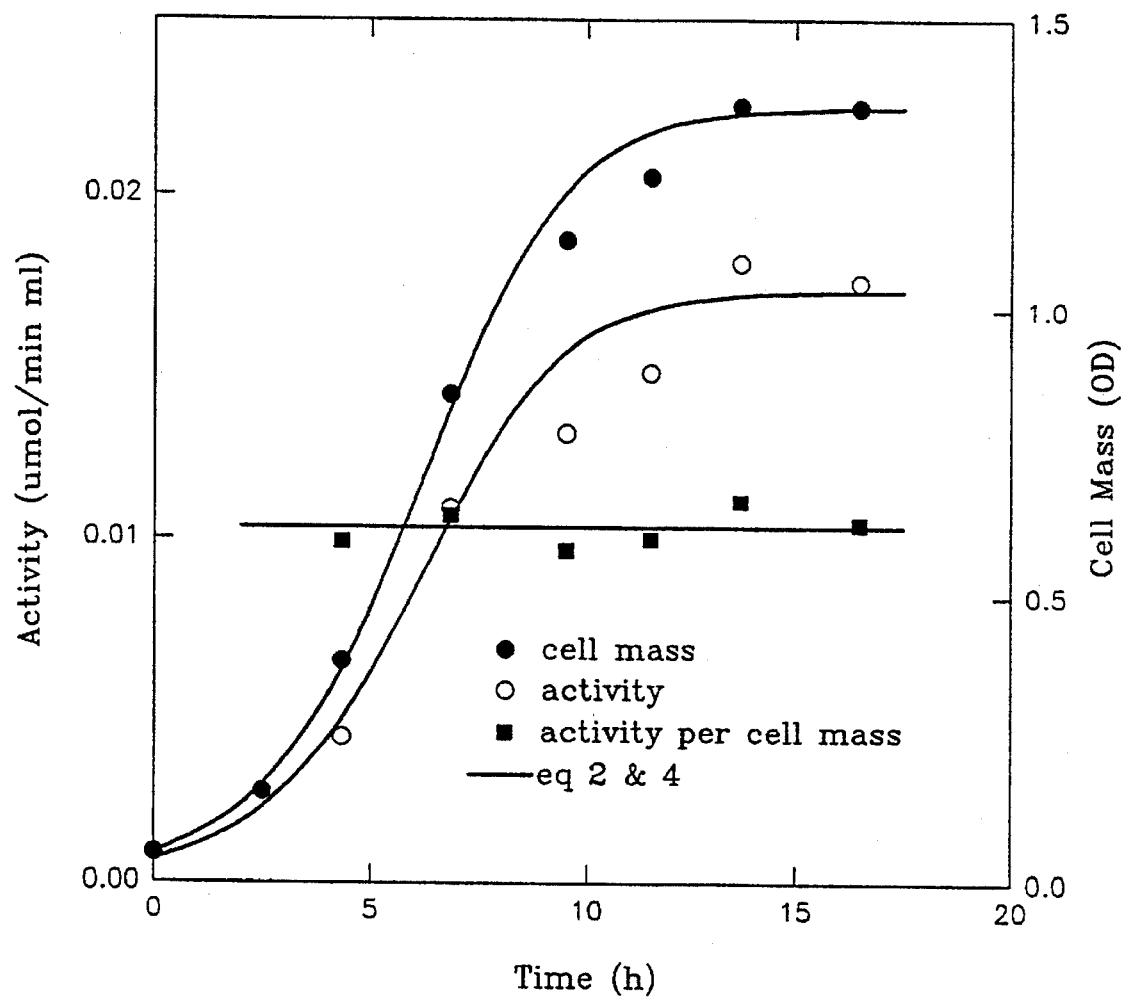
FIG. 9 provides a time course of cell mass and enzyme activity by P. aeruginosa PAO1 (pRO103) at optimized conditions (Table 2).

Kinetics of Cell Growth and Enzyme production by *P. aeruginosa* PAO1 (pRO103). A typical time course for cell growth and enzyme production is shown in FIG. 9. After a period of exponential cell growth, cell concentration became limited at a maximum cell concentration. When the initial glucose concentration was greater than 0.5%, glucose concentration did not affect the maximum cell concentration (FIG. 5) and cell growth rate. Therefore, glucose concentration was not considered in the models. Although enzyme activity per unit of cell mass was dependent on medium and cultivation conditions (FIGS. 5 and 6), it was independent of cultivation time for each batch (FIG. 9), since DDO was constitutively expressed at a constant level. The cell growth of *P. aeruginosa* PAO1 (pRO103) was modeled by equation 2, and the enzyme production was modeled by equation 4.

Enzyme formation was considered as totally growth-related. The model parameters are summarized in Table 2.

TABLE 2

Optimized cultivation conditions and model parameters for *P. aeruginosa* PA01 (pRO103)

| Property | Value |
| --- | --- |
| Glucose | 0.75% wt./vol. |
| Temperature | 37° C. |
| pH | 7.0 |
| $HgCl_2$ | 25 mg/l |
| µ (1/h) | 0.58 |
| $X_{max}$ (OD) | 1.35 |
| m | 0.0128 |
| n | 0 |

Example 4

Optimization of Fermentation Conditions for Production of 2,4-D α-Ketoglutarate Dioxygenase by Recombinant *E. coli* DH5α (DYG3)

Mathematical models. The following model was used $$P(t) = m \frac{X_0 \exp(\mu t)}{1 - \frac{X_0}{X_{max}}[1 - \exp(\mu t)]} \quad (6)$$

for enzyme formation by *E. coli* DH5α (pYG3) assuming enzyme production was not growth related (m=0):

$$P(t) = \int_{\Delta t}^{t} nX dt \quad (7)$$

in which Δt is the time delay for enzyme expression.

Growth and maintenance of *E. coli* DH5α (pYG3). *E. coli* DH5α (pYG3), a strain specifically constructed for 2,4-D detection (Example 1), was routinely maintained on LB plates with 75 mg/l of ampicillin and stored at 4° C. Yeast extract was used as a carbon and energy source for *E. coli* DH5α (pYG3) with 50 mg/l of ampicillin for selective pressure. Batch cultures of *E. coli* DH5α (pYG3) were carried out in 1000 ml flasks with 400 ml media for the optimization of media and operating condition. The media were directly inoculated by a single colony on a LB plate. The flasks were shaken on a rotary shaker at 200 rpm and incubated at 30° C. or 37° C.

Enzyme Assays. Since the membrane of *E. coli* is not permeable to 2,4-D, cell-free extracts containing the DDO produced in *E. coli* DH5α (pYG3) were used for enzyme assays. Whole cells, which were washed by sodium phosphate buffer (pH8.0), were used for enzyme assays for DDO produced by *P. aeruginosa* PA01 (pRO103).

Enzyme activity was determined from DCP concentrations after incubation at room temperature (approximately 20° C.) in 125 mg/l 2,4-D and 10 mM sodium phosphate buffer (pH 8.0) containing 100 µM ferrous ammonium sulfate and 1 mM α-ketoglutarate for 5 minutes. DCP concentration was measured by the 4-aminoantipyrine method (E. Emerson, *J. Org. Chem.* 1943, 8, 417–419). In place of 2,4-D, phenoxyacetic acid was used for *P. aeruginosa* PA01 (pRO103).

Preparation of cell-free extracts. *E. coli* cultures (10 or 15 ml) were harvested by centrifugation (8,000×g) for 10 minutes, washed using 5 ml of 100 mM sodium phosphate buffer (pH 8.0), then resuspended in 3 ml of phosphate buffer. Cell-free extracts were obtained by passing the cells once through a pre-chilled French press at 1500 psi and clarifying the debris by centrifugation (16,000×g) for 20 minutes at 4° C.

Carbon sources and concentrations. Yeast extract and glucose were tested as carbon sources. The cell growth rate on glucose was very similar to that on yeast extract. However, cells grown on glucose did not produce any enzyme with or without IPTG. When 0.2% glucose was added to the yeast extract medium, glucose also depressed the expression of tfdA. Therefore, yeast extract was selected as the carbon source for enzyme production.

Figure 10:
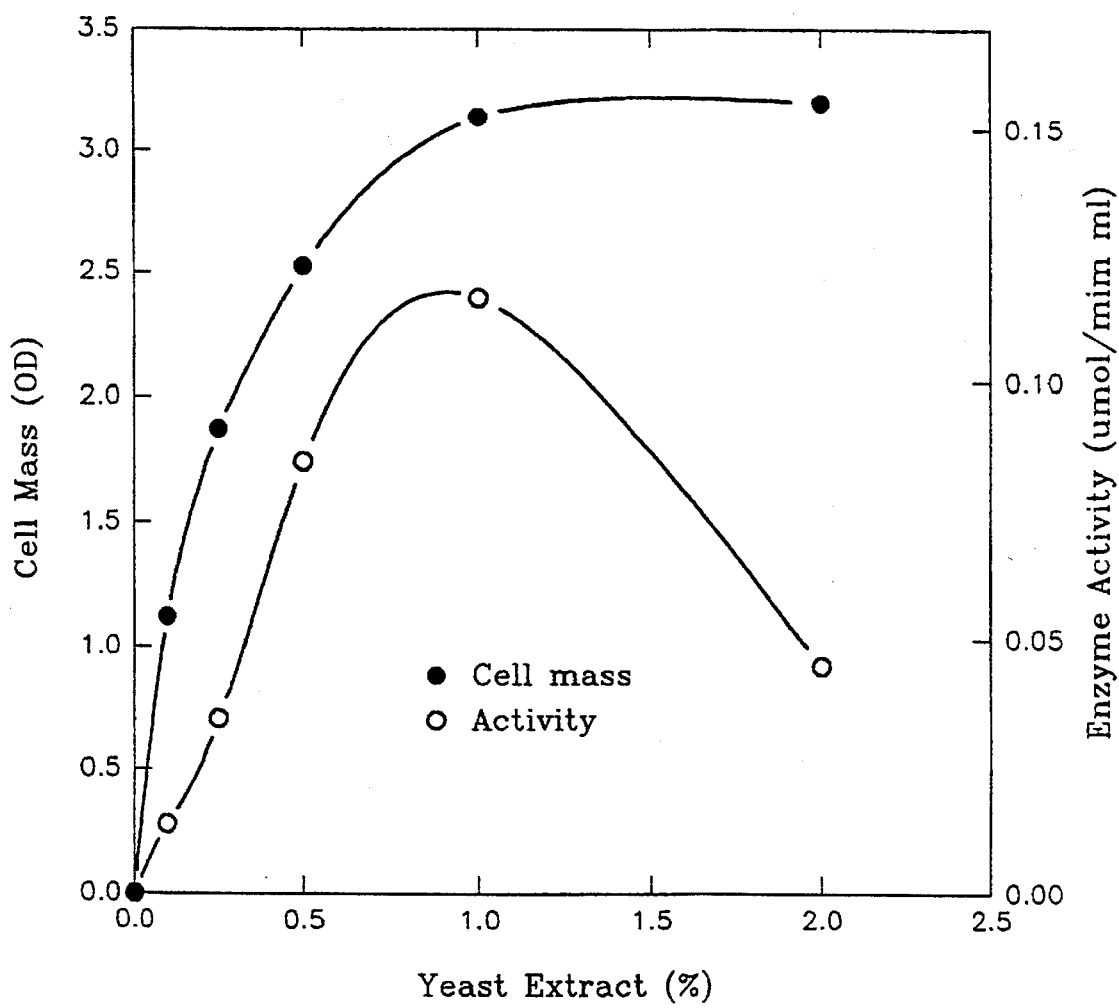
FIG. 10 plots the effects of yeast extract concentration on cell mass and enzyme activity by E. coli DH5α (pYG3).

The effects of yeast extract concentration on cell growth and enzyme formation are shown in FIG. 10. The saturation concentration for cell growth was approximately 1.0%. Below 1.0%, cell growth decreased with the decrease of yeast extract concentration. Enzyme formation was maximum at 1.0% and this concentration was selected for further study.

Figure 11:
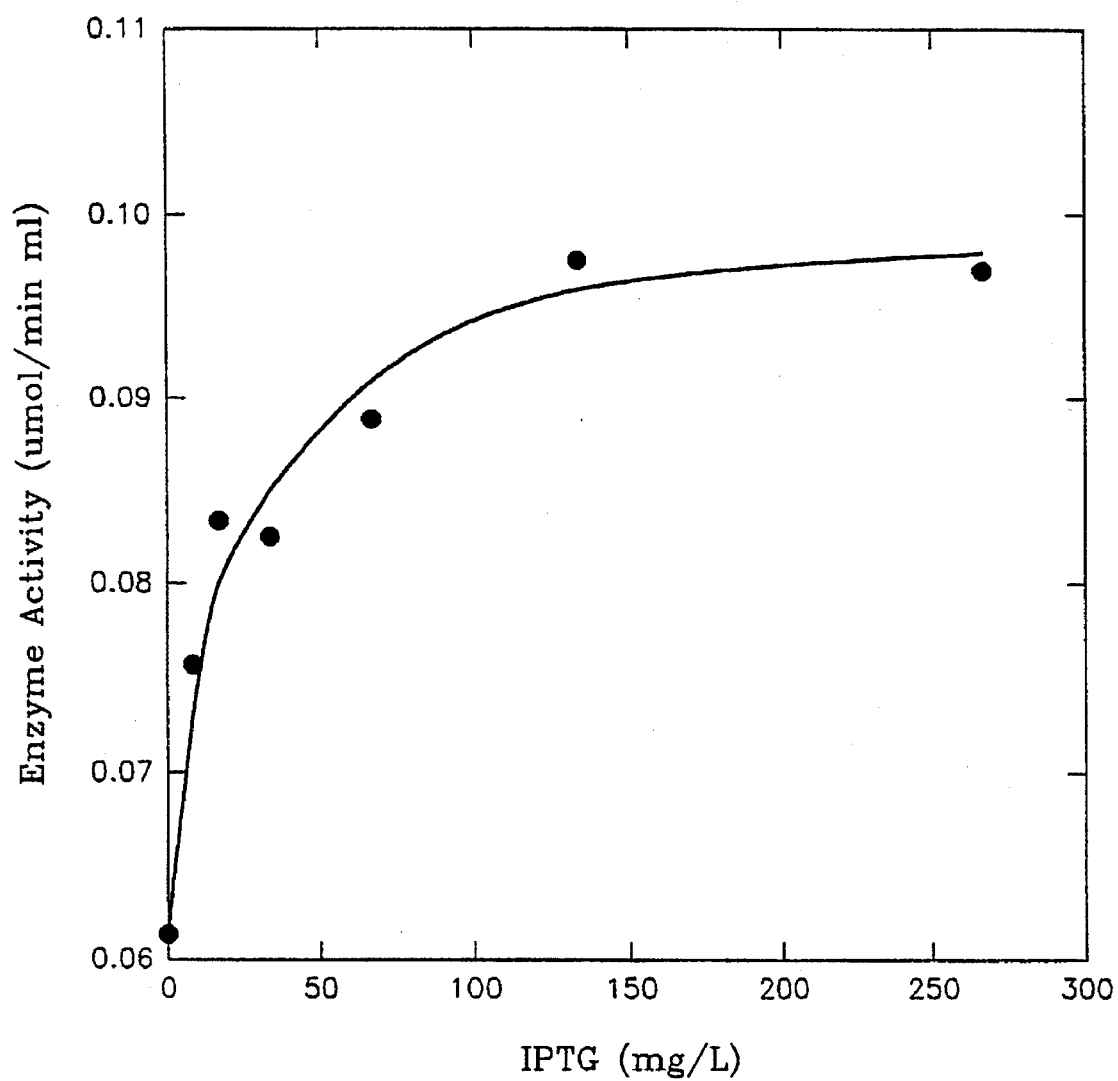
FIG. 11 plots the effect of IPTG concentration on enzyme expression by E. coli DH5α (pYG3).

IPTG concentration. IPTG was used as the inducer of the lacZ promoter which regulated the expression of tfdA in pYG3 (Example 1). The effect of IPTG concentration on enzyme production is shown in FIG. 11. The saturation IPTG concentration for this organism was approximately 150 mg/l where enzyme productivity was approximately 40% higher than without IPTG.

Without adding IPTG, tfdA was still expressed in this organism at a relatively high level. Although the promoter of tfdA has not been determined, previous work indicates that insertion of a DNA fragment into the XbaI site results in poor expression of tfdA if a foreign promoter is not provided (W. Streber et al., *J. Bacteriol.* 1987, 169, 2950–2955). Therefore, the tfdA promoter probably is near the XbaI site, which was used as a cloning site in the construction of pYG3. It is possible that the relatively high level of enzyme without IPTG was produced through mediation of a tfdA promoter. However, the lacZ promoter still increased the expression of tfdA. Another possible explanation is that the host cell cannot produce enough repressor to stop the expression of tfdA through the lacZ promoter since pYG3 is a high copy plasmid and the gene lacI is not included in pYG3.

Figure 12:
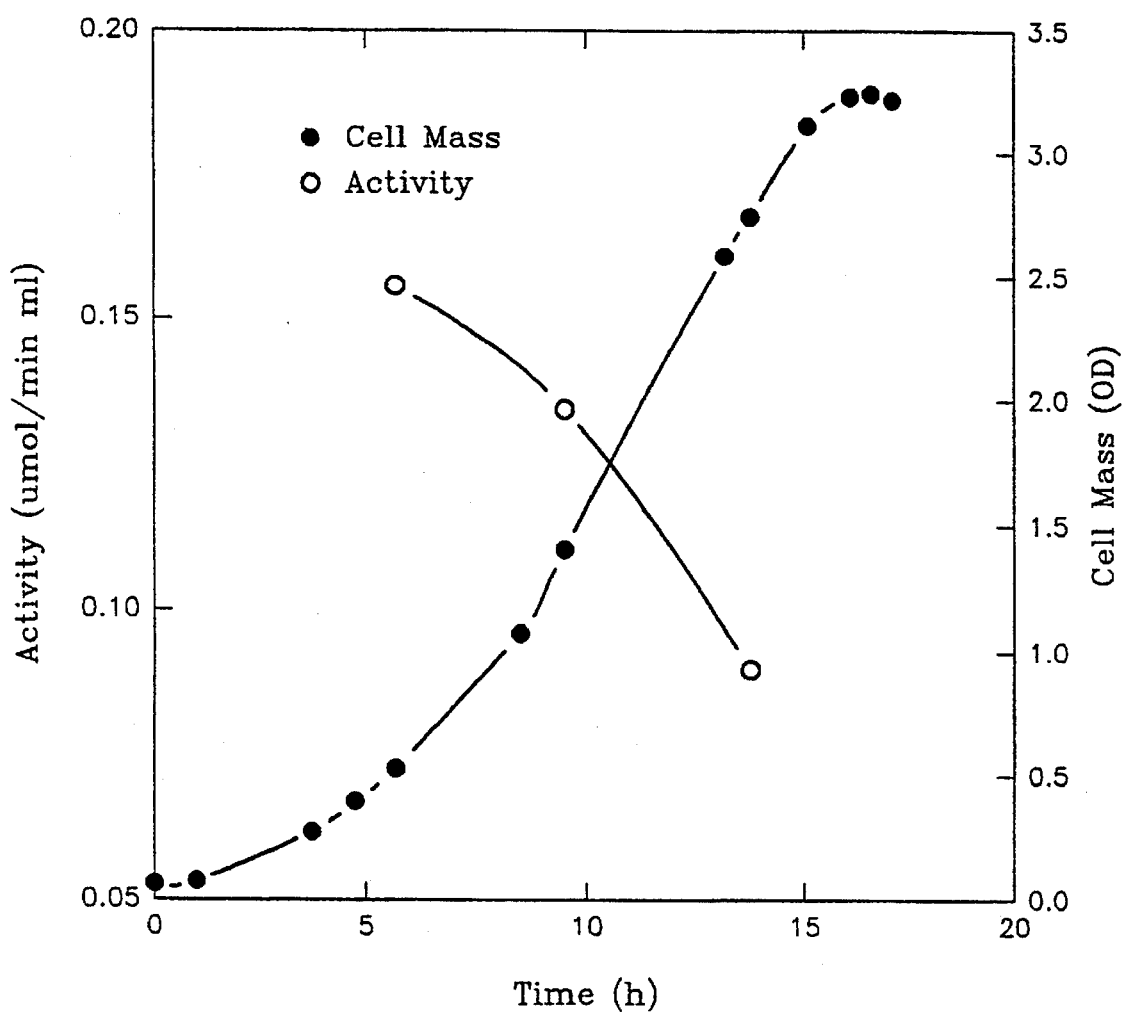
FIG. 12 plots the effects of induction time on enzyme activity by E. coli DH5α (pYG3).

Induction time. The effects of induction time on enzyme production are shown in FIG. 12. The times for the activity curve were induction times. Enzyme activities were measured at the end of the experiment (18 h). IPTG was added at different cell growth stages, early log phase (OD=0.5), middle log phase (OD=1.5) and near stationary phase (OD= 2.8). While cell growth rates for different induction times were similar, the enzyme activity of cells induced at early log phase was much higher than those induced later. Therefore, it is preferable to induce the expression of tfdA at early log phase.

Figure 13A:
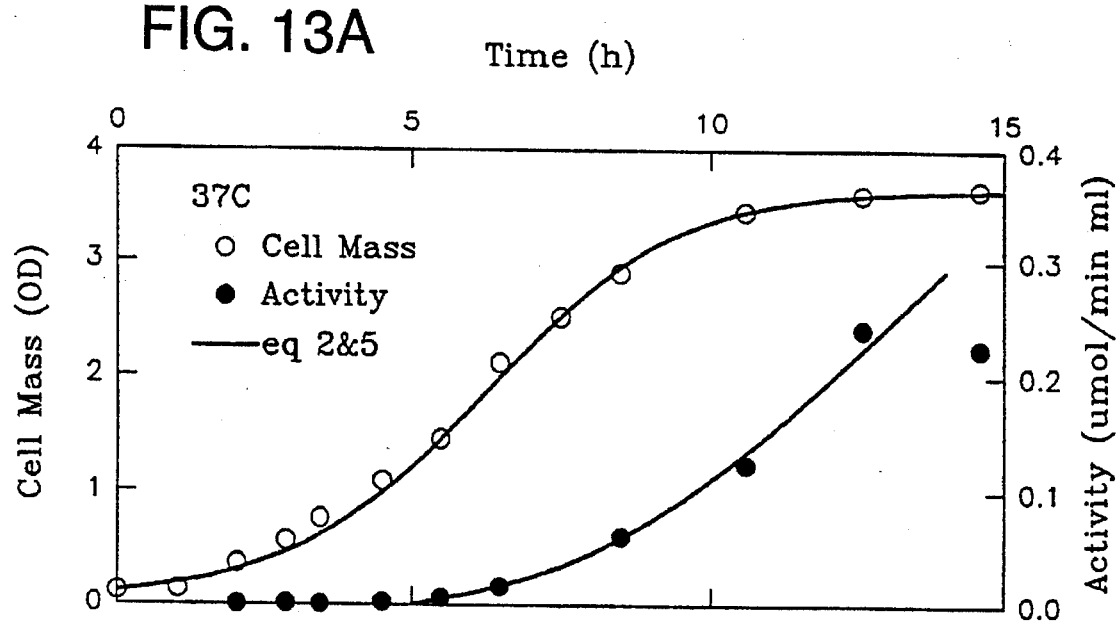
FIG. 13 shows time courses of cell mass and enzyme activity by E. coli DH5α (pYG3) at 37° C. (A) and 30° C. (B).

Temperature. The optimum cell growth temperature for *E. coli* is 37° C. However, it was previously determined that the formation of enzyme inclusion bodies in *E. coli* JM109 (pUS311) occurs at 37° C. (F. Fukumori and R. Hausinger, *J. Bacteriol.* 1993, 175, 2083–2086). At 30° C., the organism produced active DDO (F. Fukumori and R. Hausinger, *J. Bacteriol.* 1993, 175, 2083–2086). These two temperatures, 30° C. and 37° C., were investigated for the enzyme production by *E. coli* DH5α (pYG3). The results for cell growth and enzyme production are shown in FIGS. 13A nd 13B. *E. coli* DH5α (pYG3) produced active enzyme at 37° C.; enzyme productivity at 37° C. was higher than at 30° C. Therefore, 37° C. was recommended for enzyme production by *E. coli* DH5α (pYG3).

Kinetics of Cell Growth and Enzyme Production by *E. coli* DH5α pYG3). Cell growth and enzyme production by *E. coli* DH5α (pYG3) at 30° C. and 37° C. were modeled by equation 2 and equation 5. Kinetic parameters are listed in Table 3. The cell specific growth rate at 37° C. was approximately 4% higher than at 30° C., and the maximum cell concentration was also very similar. The doubling time for *E. coli* DH5α (pYG3) with enzyme expression was approximately 100 minutes, which is much longer than the doubling time of host cells. Enzyme formation is still described by the Leudeking and Piret model if a time delay (at) for enzyme expression is introduced (equation 5). The time delay is not only a parameter needed for modeling enzyme production, but also a real experimental phenomenon previously observed for inducible protein expression systems (F. Miao and D. Kompala, *Biotechnol. Bioeng.* 1992, 40, 787–796). After adding IPTG, the enzyme was not expressed immediately, but only after a time delay. The time delay changed with cultivation temperature. The time delay was 2 h at 37° C. and 0.75 h at 30° C. Because enzyme activity before induction was very low, it was assumed that the enzyme activity at induction was zero in modeling. However, this enzyme formation model was only suitable before the cells reached a stationary phase of growth. When cells reached the stationary phase, no enzyme was produced, and enzyme activity decreased with time in the stationary phase.

Figure 14:
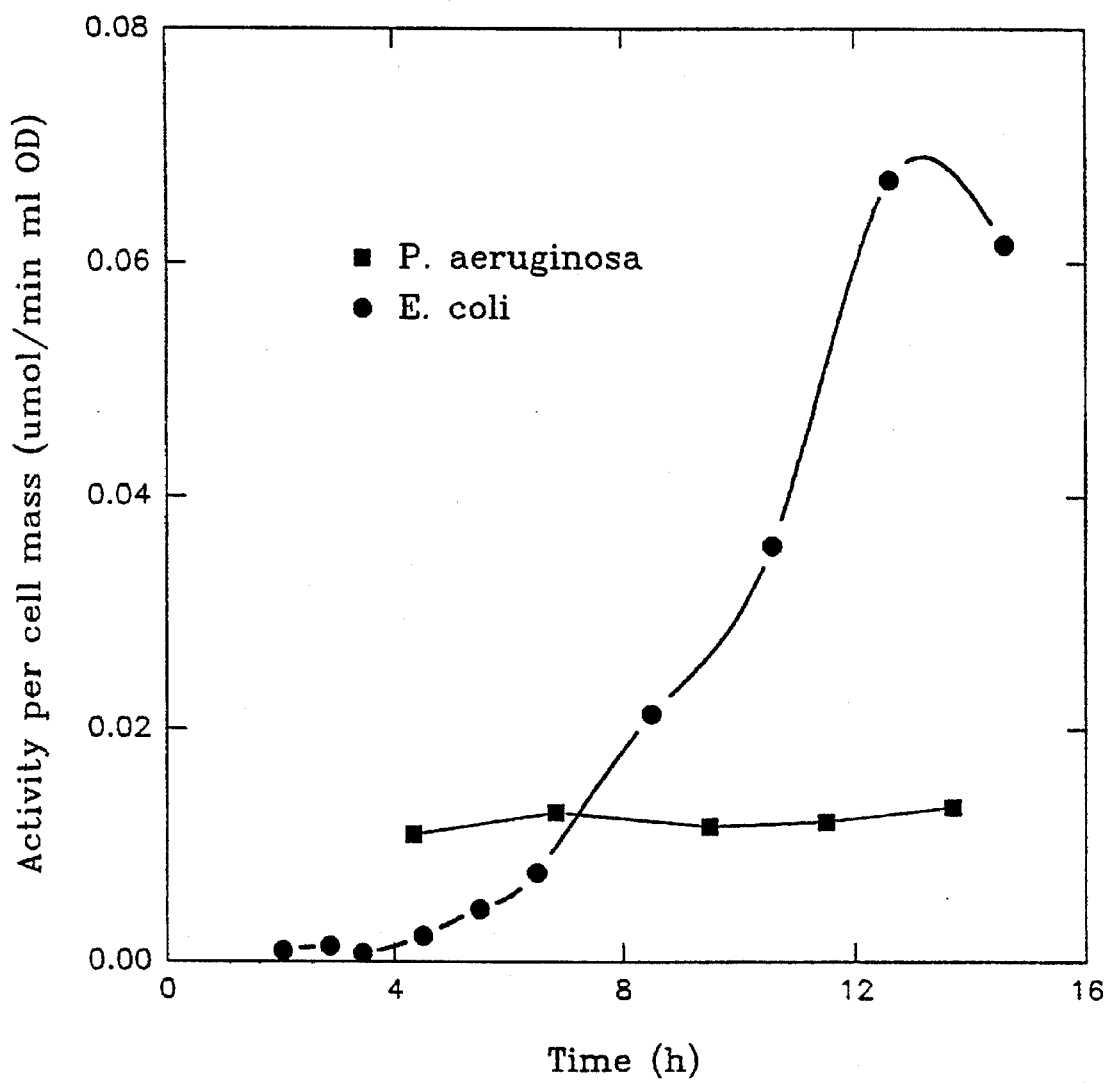
FIG. 14 is a plot comparing enzyme production by E. coli DH5α (pYG3) and P. aeruginosa PAO1 (pRO103).

The difference in enzyme production between *E. coli* DH5α (pYG3) and *P. aeruginosa* PAO1 (pRO103) is shown in FIG. 14. While the enzyme activity per cell mass of *P. aeruginosa* PAO1 (pRO103) did not change with time during batch culture, the enzyme activity per cell mass of *E. coli* DH5α (pYG3) Changed with time. Also, an inducer was needed for *E. coli* DH5α (pYG3), because tfdA was regulated in pYG3. The enzyme productivity of *E. coli* DH5α (pYG3) was approximately 10 times higher than that of *P. aeruginosa* PAO1 (pRO103).

TABLE 3

Kinetic parameters for *E. coli* DH5α (pYG3)

| Temperature | 37° C. | 30° C. |
|---|---|---|
| μ (1/h) | 0.60 | 0.52 |
| X$_{max}$ (OD) | 3.65 | 3.40 |
| m | 0 | 0 |
| n | 0.0135 | 0.0135 |
| Δt (h) | 2 | 0.75 |

Example 5

Studies on the Activity of Recombinant 2,4-D α-ketoglutarate dioxygenase

Figure 15:
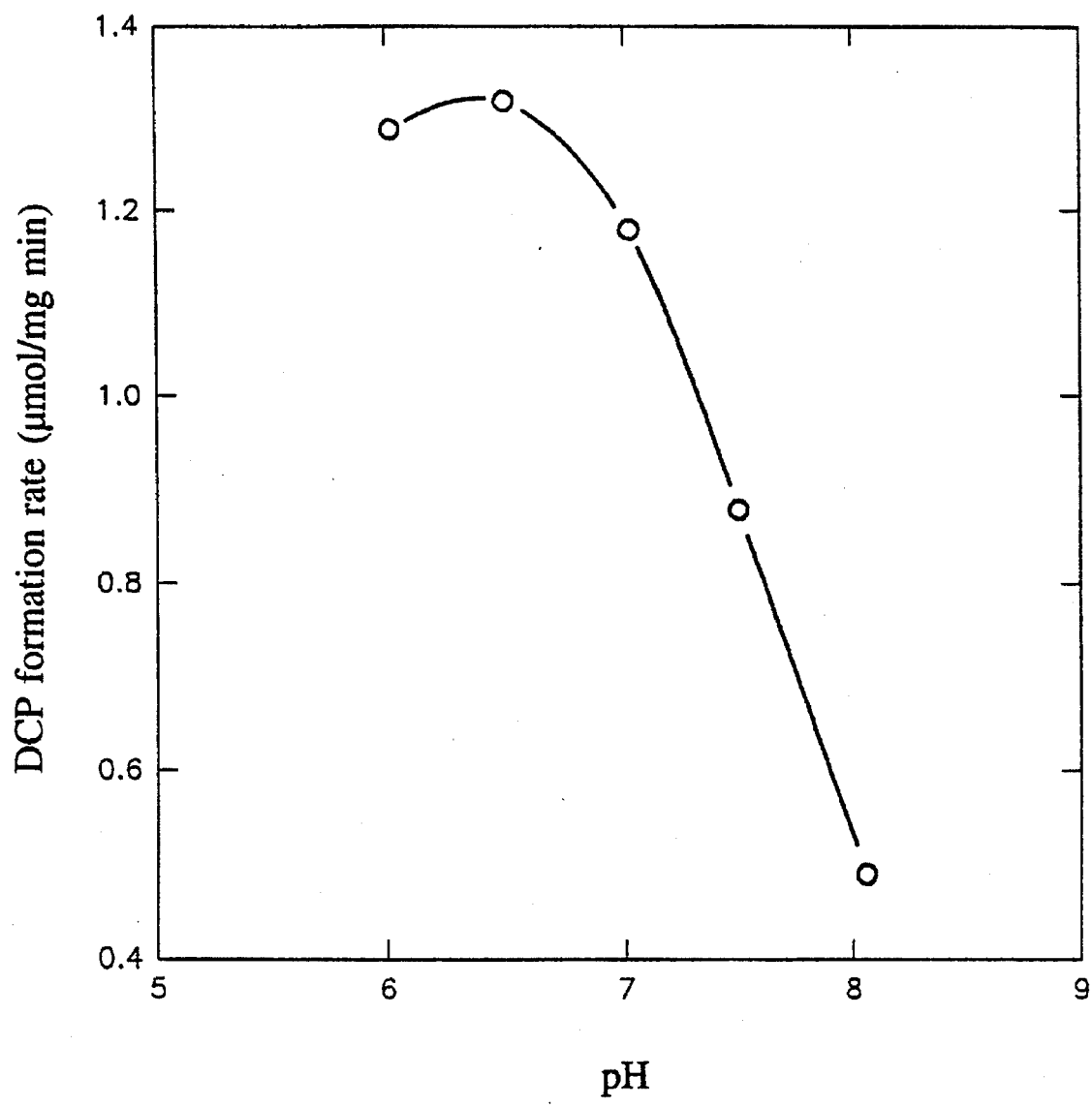
FIG. 15 plots the effect of pH on enzyme activity.

Effect of pH on enzyme activity. Since the color reaction by the 4-aminoantipyrine method is almost instantaneous, the conversion rate of 2,4-D into DCP determines the response time for 2,4-D detection. Higher reaction rates result in smaller response times or less enzyme needed for 2,4-D detection. FIG. 15 shows that pH has a strong effect on enzyme activity. The optimum pH for the enzymatic reaction is 6.5. However, the preferred pH for the color reaction is in the range of pH 8.0 to 12.0. The color is also more stable in this pH range. More importantly, 4-aminoantipyrine reacts with potassium ferricyanide at pH 6.5, producing a slight color change that is similar to having 2 mg/l DCP in solutions. Although pH 6.5 can be used for the enzymatic reaction if the pH of the solution is subsequently adjusted for the color reaction, this is less convenient. Therefore, a compromise pH 8.0 was selected for the 2,4-D detection system.

Figure 16:
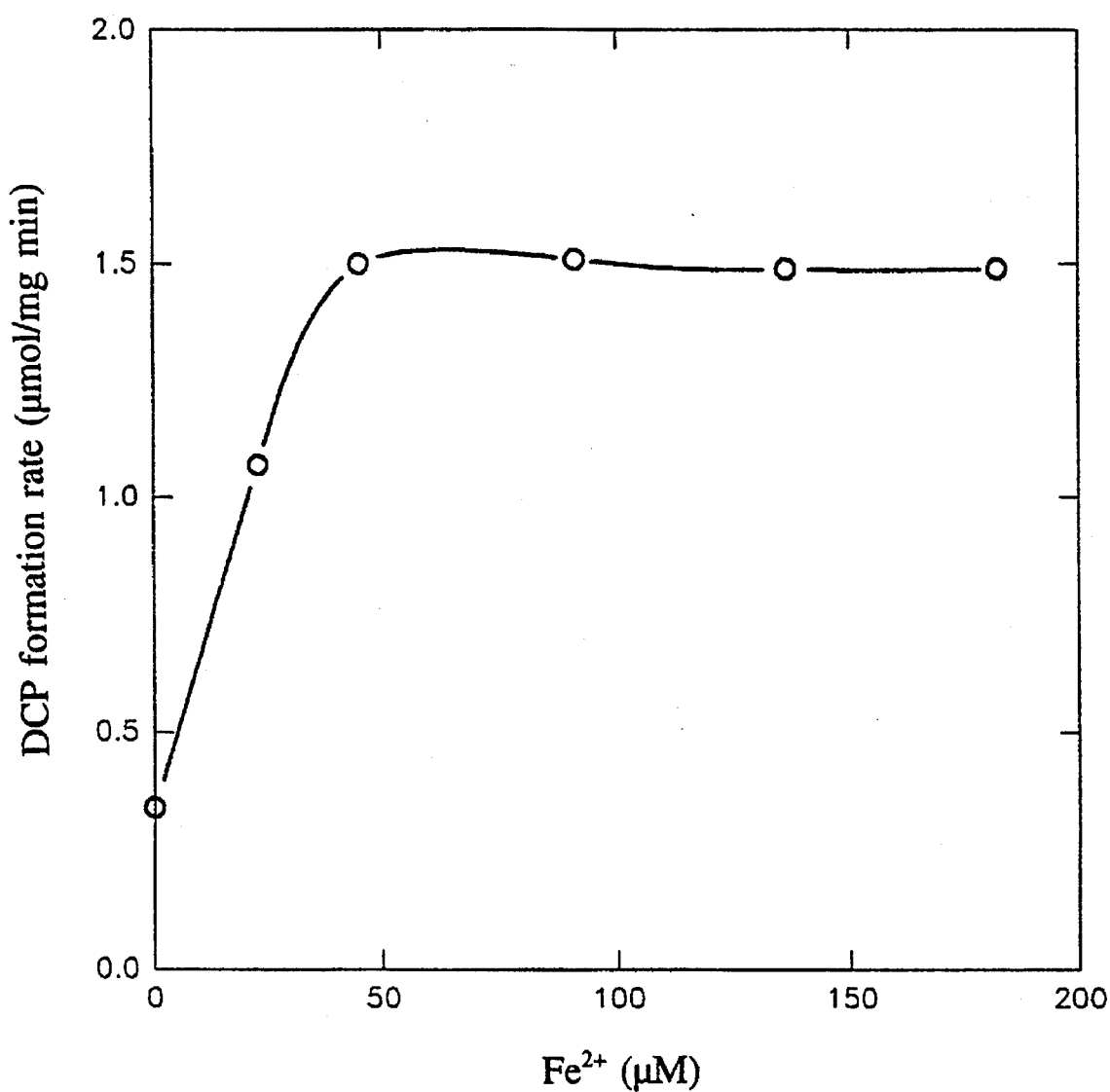
FIG. 16 plots the effect of ferrous ion concentration on enzyme activity (pH 6.5).

Effect of $Fe^{2+}$ on enzyme activity. DDO requires ferrous ion as a co-factor (F. Fukumori and R. Hausinger, *J. Bacteriol.* 1993, 175, 2083–2086). The effect of ferrous ion concentration on enzyme activity for the cell-free extract is shown in FIG. 16. Enzyme activity increased approximately 5-fold by adding ferrous ions up to 50 μM. This saturation concentration should be a function of enzyme concentration used. In order to maximize enzyme activity, a higher ferrous ion concentration, such as 100 μM, should be used for 2,4-D detection.

Figure 17A:
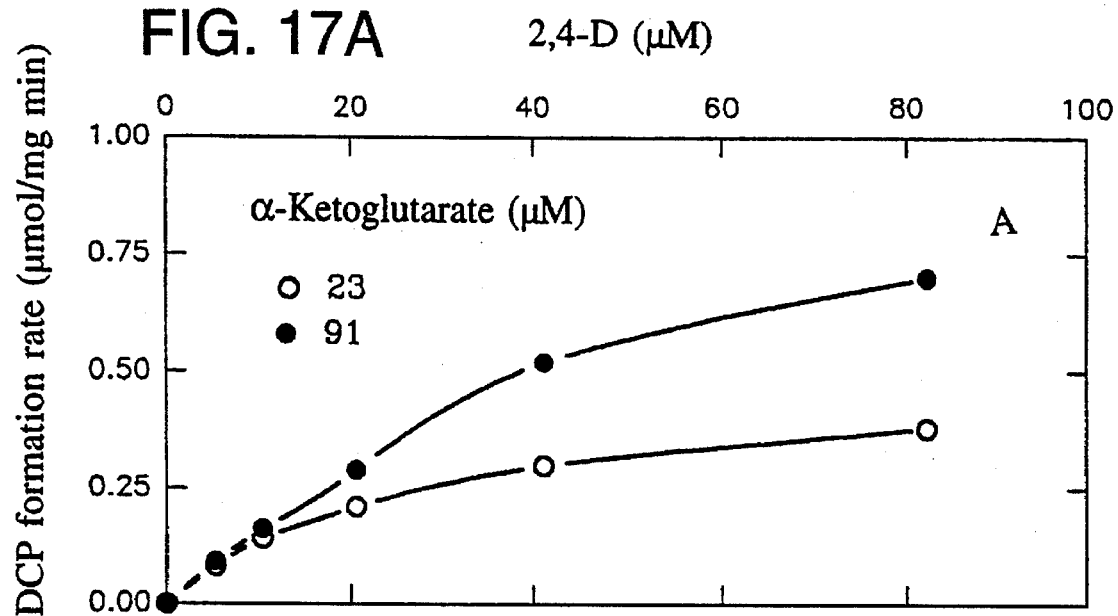
FIG. 17 plots the effects of 2,4-D (A) and α-ketoglutarate (B) on 2,4-DCP production rate.
Figure 17B:
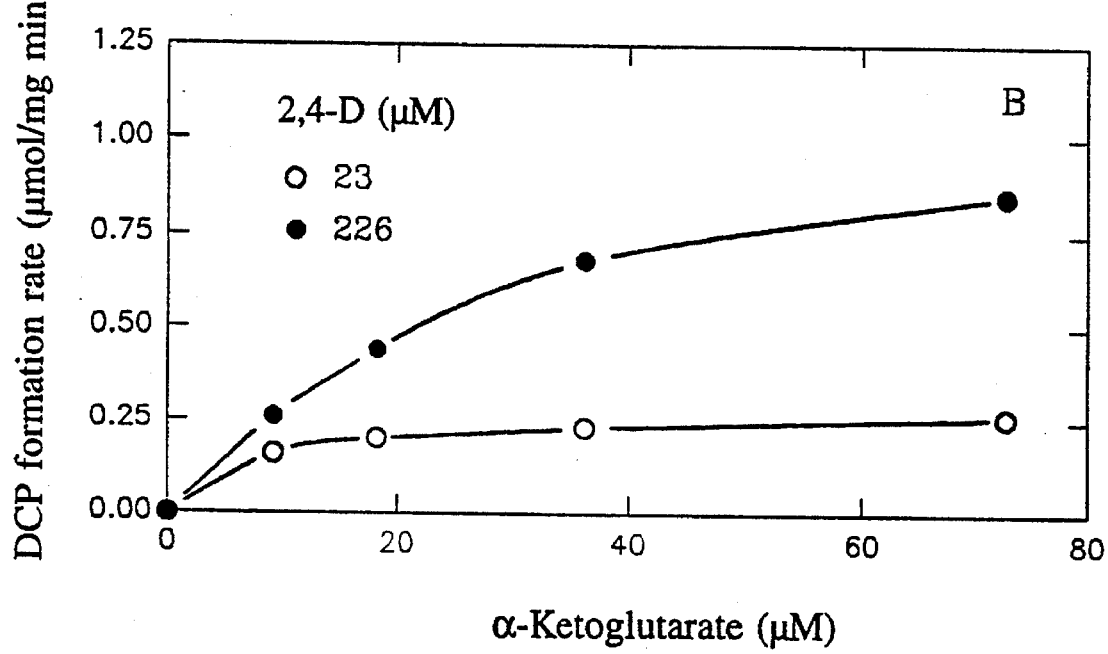

Effects of α-ketoglutarate and 2,4-D concentration on DCP production rates. Previously, the conversion of 2,4-D into DCP was thought to be catalyzed by a monooxygenase (W. Streber et al., *J. Bacteriol.* 1987, 169, 2950–2955). However, recent study has shown that this reaction is catalyzed by an α-ketoglutarate-dependent dioxygenase with oxygen and α-ketoglutarate required as co-substrates (F. Fukumori and R. Hausinger, *J. Bacteriol.* 1993, 175, 2083–2086). Although it is not practical to control oxygen concentration for 2,4-D detection, α-ketoglutarate concentration can be optimized. The effects of α-ketoglutarate and 2,4-D concentrations on DCP production rate are shown in FIGS. 17A and 17B, respectively. The concentration of α-ketoglutarate for 23 μM of 2,4-D was approximately 10 μM, while the saturation concentration for 226 μM of 2,4-D was greater than 70 μM. Since 10 mg/l of DCP is sufficient for 2,4-D detection, 1 mM α-ketoglutarate is sufficient for 2,4-D detection.

Figure 18A:
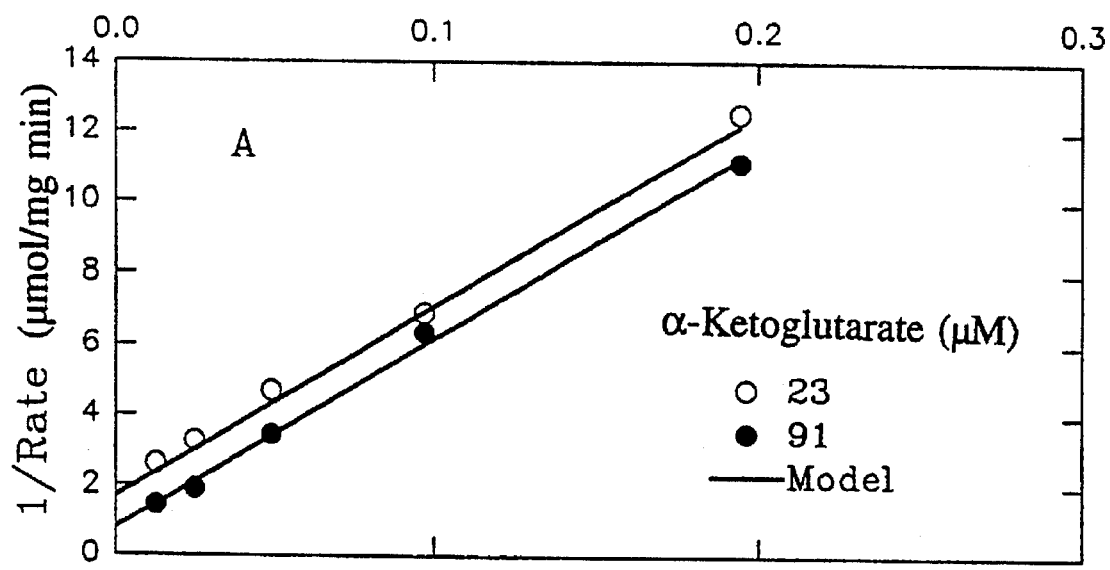
FIG. 18 is a pair of Lineweaver-Burke plots for DCP production at different 2,4-D (A) or α-ketoglutarate (B) concentrations.
Figure 18B:
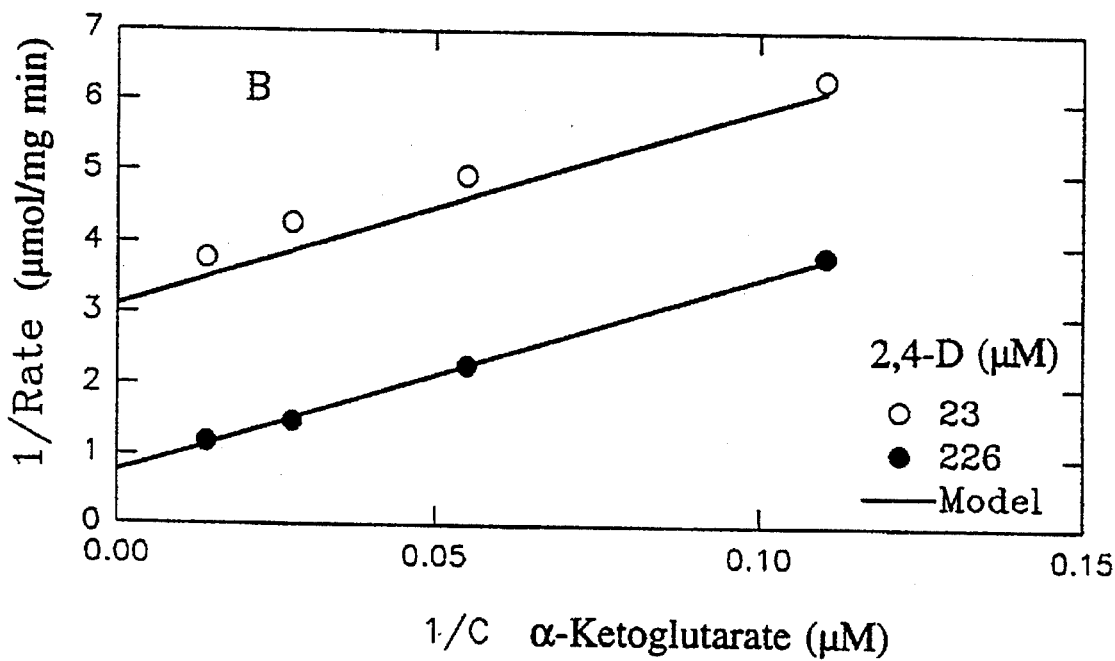

Kinetics of enzymatic reaction. There are three substrates, 2,4-D, α-ketoglutarate and oxygen, in the enzymatic reaction in which 2,4-D is oxidized to DCP (F. Fukumori and R. Hausinger, *J. Bacteriol.* 1993, 175, 2083–2086). Since oxygen cannot be controlled in the process of 2,4-D detection, oxygen was not considered in the model. Kinetic data were measured at pH 8.0, 100 mM $Fe^{2+}$ and room temperature (20° C.), as shown in the Lineweaver-Burk plots in FIGS. 18A and 18B.

Clearly, the enzymatic reaction has a Ping Pong Bi Bi mechanism with respect to 2,4-D and α-ketoglutarate (D. Voet and J. Voet, 1990. *Biochemistry*. John Wiley & Sons, New York, pp. 347–348). Kinetic parameters obtained from the rate data are listed in Table 4. The kinetic model can be directly applied to the quantitative design of a 2,4-D detection system using the cell-free extract.

The reaction rate can be expressed as (D. Voet and J. Voet, 1990. *Biochemistry*. John Wiley & Sons, New York):

$$\frac{1}{v_o} = \frac{K_M^{2,4-D}}{V_{max}[2,4-D]} + \frac{K_M^{\alpha-KG}}{V_{max}[\alpha-KG]} + \frac{1}{V_{max}} \quad (8)$$

where $v_o$ is the reaction rate, [2,4-D] is 2,4-D concentration, [α-KG] is α-ketoglutarate concentration, and $V_{max}$, $K_M^{2,4-D}$ and $K_M^{\alpha-KG}$ are model parameters. The values of model parameters were determined from double reciprocal plots.

TABLE 4

Enzyme parameters determined from kinetic models*

| Parameters | Value |
|---|---|
| $V_{max}$ (μmol/min mg) | 2.0 |
| $K_M^{2,4-D}$ (μM) | 107 |
| $K_M^{\alpha-KG}$ (μM) | 55 |

*at 20° C., pH 8.0, 50 μM $Fe^{2+}$

Example 6

Figure 19:
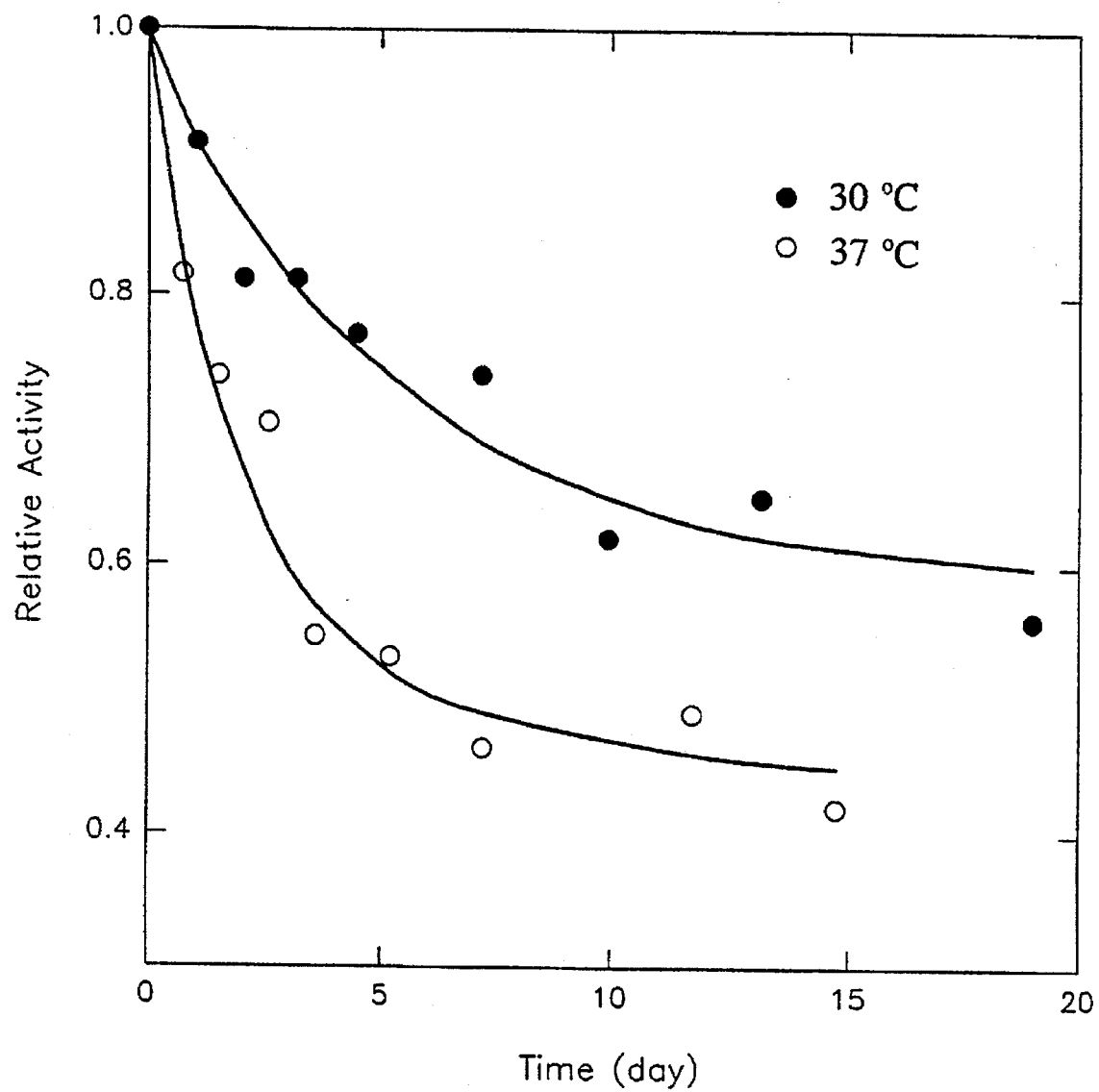
FIG. 19 plots the stability of dried enzyme samples at 37° C. and 30° C.

Use of the Dried Recombinant 2,4-D α-ketoglutarate dioxygenase for 2,4-D Detection For practical 2,4-D detection methods, enzyme stability is important. Since the dried enzyme is intended to be used in 2,4-D detection, only the stability of the dried enzyme was examined. Samples were prepared by adding cell-free extracts to small filter bags (0.7 cm×8 cm) and drying under vacuum at room temperature for 3 hours. Cell-free extract protein (50 μg) was used for each sample. The dried samples of cell-free extract were stored at different temperatures, and activity was measured periodically. The results are shown in FIG. 19. After a period of activity decrease, the activity of dried cell-free extract in the filter bag reached a stable value.

Example 7

2,4-D Detection Kit

A kit for 2,4-D detection has been developed. The kit includes the following items:

1) 5 mM $Fe(NH_4)_2(SO_4)_2$ solution;
2) 100 mM α-ketoglutarate solution;
3) 40 mM 4-aminoantipyrine solution;
4) 8% wt/vol potassium ferricyanide solution;
5) dried 2,4-D α-ketoglutarate dioxygenase in filter bags or immobilized on a solid support, such as a dipstick or beads.

2,4-D α-ketoglutarate dioxygenase is the enzyme which converts 2,4-D into DCP. $Fe^{2+}$ is used as a co-factor by the enzyme and α-ketoglutarate is a co-substrate for the 2,4-D conversion reaction. 4-Aminoantipyrine and potassium ferricyanide are reagents for the color reaction. Each of the reagents may be provided in a separate container. The reaction conditions and amounts of the solutions used for each detection are summarized in Table 5.

If the pH of water samples is about pH 7, pH 8.0 can be automatically achieved by the buffer ingredients in the cell-free extract. Otherwise, a pH adjustment of water samples, e.g., by addition of a physiologically compatible pH 7.0 to 8.0 buffer solution, including but not limited to Tris-HCL, HEPES, or bicarbonate, may be required. In order to improve the stability of the detection kit, the amount of enzyme used for each sample was adjusted to twice that used in enzyme stability measurements (100 μg protein for each sample).

This 2,4-D detection kit was designed for the unassisted visual detection of the presence of 2,4-D in a test sample. After adding 4-aminoantipyrine and potassium ferricyanide solution, the color formed from a 2 mg/l DCP solution was slightly red, which could be easily distinguished from the color of a control (bright yellow). However, the color formed from 10 mg/l DCP solution was dark red and could not be distinguished from the color formed from DCP solutions at higher concentrations.

The concentration of DCP converted from 2,4-D in this detection kit was affected by 2,4-D concentration, enzyme activity and amount, α-ketoglutarate and $Fe^{2+}$ concentration and reaction time. With the values recommended in Table 5, longer reaction times can be used to increase DCP concentration and thereby increase 2,4-D detection sensitivity.

The procedure used in determining the values included in Table 5 was as follows: To 1 ml of 2,4-D containing sample (adjust pH if necessary) add 10 μl of 5 mM $Fe(NH_4)_2(SO_4)_2$, 10 μl of 100 mM α-ketoglutarate, and enzyme (dried in a filter paper bag). Incubate at room temperature (~20° C.) for 10 minutes. Add 10 μl of 40 mM 4-aminoantipyrine and 5 μl of 8% wt. potassium ferricyanide. Score positive (+) ($\geq 2$ ppm 2,4-D) if red, score negative (−) if yellow (<2 ppm 2,4-D).

TABLE 5

Summary of recommended conditions and procedure for 2,4-D detection

| Reaction Conditions | Recommended Value |
| --- | --- |
| Volume (water sample containing 2,4-D) | 1 ml |
| Reaction temperature | room temperature (~20° C.) |
| pH | 8.0 |
| $Fe(NH_4)_2(SO_4)_2$ | 50 μM |
| α-Ketoglutarate | 1 mM |
| Reaction time | $\geq 10$ min |
| 40 mM 4-aminoantipyrine | 10 μl |
| 8% wt. potassium ferricyanide | 5 μl |
| Protein amount for each sample (dried) | 100 μg |
| Enzyme storage temperature | 4° C. or room temperature |

The stability of this 2,4-D detection kit was examined experimentally using a solution of 10 mg/l 2,4-D and a reaction time of 10 minutes. All solutions and the enzyme were stored at room temperature (approximately 20° C.). 4-aminoantipyrine was stored in a brown bottle because it is light sensitive. The stability of this kit is shown in Table 6.

A similar DCP concentration was produced by this detection system throughout the 13-week test period. FIG. 19 shows that enzyme stability was greater at lower temperatures. Therefore, it is expected that the shelf life of this 2,4-D detection kit will be extended when it is stored at 4° C., e.g., in a refrigerator, or in a cool dark place.

TABLE 6

Stability of 2,4-D detection system*

| Time (week) | $OD_{510}$ |
| --- | --- |
| 0 | 0.56 |
| 1 | 0.52 |
| 2 | 0.54 |
| 3 | 0.67 |
| 4 | 0.61 |
| 5 | 0.68 |
| 6 | 0.64 |
| 8 | 0.69 |
| 10 | 0.63 |
| 13 | 0.48 |
| 15 | 0.35 |

Example 8

Dipstick Bioassay

A bacterial strain producing recombinant DDO is grown to log phase, harvested and washed, then immobilized on the surface of a "dipstick" wafer. The immobilized cells are preserved by drying. Alternatively, a crude cell-free lysate or more purified forms of the enzyme may be used. The DDO is hydrated and thus reactivated simply by wetting the wafer.

The dipstick wafer containing the immobilized cells is wetted with a known volume of a sample (e.g., agricultural rinse water) to be tested for the presence of 2,4-D. After a short incubation period (e.g., 30–60 minutes at room temperature) to allow for bacterial cleavage of the 2,4-D to produce dichlorophenol, the dichlorophenol is detected by a procedure including (1) application of one drop of 8% ferricyanide to the dipstick, (2) air drying, and (3) application of one drop of a colorimetric detection reagent (pH 10 buffer/2% aminoantipyrine/8% potassium ferricyanide at a 5:1:1 ratio). Color develops rapidly and in proportion to the original amount of 2,4-D presented in the sample. The color of the dipstick is compared to a chart of color standards of intensity versus 2,4-D concentration. The sensitivity is expected to be 0.1–2.0 ppm. Specificity is very high, since the detected product is produced by a very specific enzyme reaction.

All publications and published patent documents cited in this specification are incorporated herein by reference to the same extent as if each individual publication or patent application was specifically and individually indicated to be incorporated by reference.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

What is claimed is:

1. A method for detecting the presence of a phenoxy ether compound in a sample, the method comprising the steps of:

providing a dried enzyme preparation that comprises an enzyme having an activity when hydrated of cleaving a phenoxy ether bond of the compound to produce a phenolic product and that maintains the activity after storage at approximately 20° C. for at least three months;

hydrating the dried enzyme, thereby producing a hydrated enzyme;

contacting the sample with the hydrated enzyme under conditions compatible with activity of the enzyme; and detecting the presence of the phenolic product.

2. A method according to claim 1 wherein the presence of the phenolic product is detected by an assay comprising reacting the phenolic product with 4-aminoantipyrine and potassium ferricyanide.

3. A method according to claim 1 wherein the compound is selected from the group consisting of: 2,4-dichlorophenoxyacetic acid; 3,6-dichloro-2-methoxybenzoic acid; 4-chloro-2-methyl-phenoxyacetic acid; phenoxyacetic acid, 2-(2,4-dichlorophenoxy)propionic acid; 2-(4-chloro-2-methylphenoxy)-propionic acid; (2,4,5,-trichlorophenoxy)acetic acid; 2,3-dihydro-2,2-dimethyl-7-benzofuranyl methylcarbamate; p-chlorophenyl benzenesulfonate; p-chlorophenyl p-clorobenzenesulfonate; 2-(p-tert-butylphenoxy)cyclohexyl 2-propynyl sulfite; 1-naphtyl methylcarbamate; o,o-dimethyl o-2,4,5-trichlorophenyl methylphosphorothioate; 4-tert-butyl-2-chlorophenyl methyl-methylphosphoroamidate; o,o-dimethyl o-2-chloro-1-(2,4,5-trichlorophenyl) vinyl phosphate; o-(4-bromo-2-chlorophenyl)-o-ethyl-S-propyl phosphorothioate; o-ethyl S-propyl o-(4-methylthio) phenyl phosphorodithioate; 1-methylethyl 2-([ethoxy (1-methyl-ethyl) amino phosphinothioyl] oxy)benzoate; o,o-diethyl O-(2-isopropyl-4-methyl-6-pyrimidinyl) phosphorothioate; o,o-diethyl o-(3, 5,6-trichloro-2-pyridyl) phosphorothioate; 1,1,1-trichloro-2, 2-bis(p-methoxyphenyl)ethane; butyl 2-(4-(5-trifluoromethyl-2-pyridyloxy)phenoxy) propionate; (±)-2-[4-[(6-chloro-2-benzoxazolyl)oxy]phenoxy]propanoic acid; 2-(4-(2,4-dichlorophenoxy-phenoxy)-methylpropanoate; (±)-2-[4-(6-chloro-2-quinoxalinyloxy)phenoxy]propanoic acid; 4-dimethylamino-3,5-zylyl N-methylcarbamate; 2-sec-butyl-4,6-dinitrophenyl 3-methyl-2-butenoate; 2-(1-methylheptyl)-4,6-dinitrophenyl crotonate; 1-naphthyl N-methylcarbamate; [(3,5,6-trichloro-2-pyridinyl)oxy] acetic acid; [3-dimethylamino-(methyleneiminophenyl)]-N-methylcarbamate hydrochloride; 4-(methylthio)3,5-xylyl methylcarbamate (Methiocarb, Mesurol®); 4-(dimethylamino)-3-methylphenol methylcarbamate; 2-(α-naphthoxy)-N,N-diethylpropionamide; o-isopropoxyphenyl methylcarbamate; 2,2-dimethyl-1,3-benzo dioxol-4-yl methylcarbamate; 2-( 2,4,5-trichlorophenoxy)propionic acid; [(4-chloro-o-tolyl)oxy]acetic acid; Chloroneb; [(4-amino-3,5-dichloro-6-fluoro-2-pyridinyl)oxy] acetic acid; (±)-2-[4-[[3-chloro-5-(trifluoromethyl)-2-pyridinyl]oxy] phenoxy]propanoic acid; and amine, ester, and other derivatives thereof.

4. A method according to claim 3 wherein the compound is a selected from the group consisting of 2,4-dichlorophenoxyacetic acid, amine derivatives of 2,4-dichlorophenoxyacetic acid, ester derivatives of 2,4-dichlorophenoxyacetic acid, 4-chloro-2-methylphenoxyacetic acid, 2-methylphenoxyacetic acid, and phenoxyacetic acid.

5. A method according to claim 4 wherein the compound is 2,4-dichlorophenoxyacetic acid and the phenolic product is 2,4-dichlorophenol.

6. A method according to claim 1 wherein the dried enzyme is a 2,4-D α-ketoglutarate dioxygenase.

7. A method according to claim 6 wherein the step of providing the dried 2,4-D α-ketoglutarate dioxygenase comprises providing a dried cell, the cell comprising the 2,4-D α-ketoglutarate dioxygenase.

8. A method according to claim 6 wherein the cell comprises a recombinant nucleic acid that encodes the 2,4-D α-ketoglutarate dioxygenase.

9. A method according to claim 6 wherein the step of providing the dried 2,4-D α-ketoglutarate dioxygenase comprises providing a dried crude lysate of a cell, the cell comprising the 2,4-D α-ketoglutarate dioxygenase.

10. A method according to claim 9 wherein the cell comprises a recombinant nucleic acid that encodes the 2,4-D α-ketoglutarate dioxygenase.

11. A method according to claim 1 wherein the dried enzyme is immobilized on a solid support.

12. A method according to claim 11 wherein the solid support is selected from the group consisting of a bead and a dipstick.

13. A method for detecting the presence in a sample of a compound selected from the group consisting of 2,4-dichlorophenoxyacetic acid and a derivative of 2,4-dichlorophenoxyacetic acid, the method comprising the steps of:

providing a dried 2,4-D α-ketoglutarate dioxygenase having an activity when hydrated of cleaving a phenoxy ether bond of the compound to produce a phenolic product and that maintains the activity after storage at approximately 20° C. for at least three months;

hydrating the dried 2,4-D α-ketoglutarate dioxygenase, thereby producing a hydrated 2,4-D α-ketoglutarate dioxygenase;

contacting the sample with the hydrated 2,4-D α-ketoglutarate dioxygenase under conditions compatible with activity of the 2,4-D α-ketoglutarate dioxygenase, thereby producing a phenolic product; and detecting the presence of the phenolic product by an assay comprising reacting the phenolic product with 4-aminoantipyrine and potassium ferricyanide.

14. A method according to claim 13 wherein the step of providing the dried 2,4-D α-ketoglutarate dioxygenase comprises providing a dried cell, the cell comprising the 2,4-D α-ketoglutarate dioxygenase.

15. A method according to claim 14 wherein the cell comprises a recombinant nucleic acid that encodes the 2,4-D α-ketoglutarate dioxygenase.

16. A method according to claim 13 wherein the step of providing the dried 2,4-D α-ketoglutarate dioxygenase comprises providing a dried crude lysate of a cell, the cell comprising the 2,4-D α-ketoglutarate dioxygenase.

17. A method according to claim 16 wherein the cell comprises a recombinant nucleic acid that encodes the 2,4-D α-ketoglutarate dioxygenase.

18. A method according to claim 17 wherein the compound is 2,4-dichlorophenoxyacetic acid and the phenolic product is 2,4-dichlorophenol.

19. A method for detecting the presence in a sample of a compound selected from the group consisting of 3,6-dichloro-o-anisic acid and a derivative of 3,6-dichloro-o-anisic acid in a sample, the method comprising the steps of:

providing a dried 2,6-dichloro-2-methoxy-benzoic acid mono-oxygenase;

hydrating the dried 2,6-dichloro-2-methoxybenzoic acid mono-oxygenase, thereby producing a hydrated 2,6-dichloro-2-methoxy-benzoic acid mono-oxygenase;

contacting the sample with the hydrated 2,6-dichloro-2-methoxy-benzoic acid mono-oxygenase under conditions compatible with activity of the hydrated 2,6-dichloro-2-methoxy/benzoic acid mono-oxygenase, thereby converting the compound in the sample to a phenolic product; and detecting the presence of the phenolic product by an assay comprising reacting the phenolic product with 4-aminoantipyrine and potassium ferricyanide.

20. A composition for detecting the presence of a phenoxy ether compound in a sample, the composition comprising a dried enzyme preparation immobilized on a solid support, the preparation comprising an enzyme having an activity when hydrated of cleaving a phenoxy ether bond of the compound to produce a phenolic product, and that maintains the activity after storage at approximately 20° C. for at least three months.

21. A composition according to claim 20 wherein the enzyme is a 2,4-D α-ketoglutarate dioxygenase.

22. A composition according to claim 21 wherein the dried enzyme preparation is a cell, the cell comprising the 2,4-D α-ketoglutarate dioxygenase.

23. A composition according to claim 22 wherein the cell comprises a recombinant nucleic acid that encodes the 2,4-D α-ketoglutarate dioxygenase.

24. A composition according to claim 21 wherein the dried enzyme preparation is a crude lysate of a cell, the cell comprising a recombinant nucleic acid that encodes 2,4-D α-ketoglutarate dioxygenase.

25. A composition according to claim 20 wherein the solid support is selected from the group consisting of a bead and a dipstick.

26. A composition for detecting the presence of a phenoxy ether compound in a sample, the composition comprising a dried cell or crude lysate of the cell immobilized on a solid support, wherein the cell comprises a recombinant nucleic acid that encodes 2,4-D α-ketoglutarate dioxygenase and the composition can detect the presence of the compound after storage of the composition at approximately 20° C. for at least three months.

27. A kit for detecting the presence of a phenoxy ether compound in a sample, the kit comprising:

a dried enzyme preparation comprising an enzyme having an activity, when hydrated, of cleaving a phenoxy ether bond of the compound to produce a phenolic product under conditions compatible with activity of the enzyme and that maintains the activity after storage at approximately 20° C. for at least three months;

4-aminoantipyrine;

potassium ferricyanide; and instructions for use.

28. A kit according to claim 27 wherein the enzyme is a 2,4-D α-ketoglutarate dioxygenase.

29. A kit according to claim 28 wherein the dried enzyme preparation is a cell, the cell comprising the 2,4-D α-ketoglutarate dioxygenase.

30. A kit according to claim 29 wherein the cell comprises a recombinant nucleic acid that encodes the 2,4-D α-ketoglutarate dioxygenase.

31. A kit according to claim 28 wherein the dried enzyme preparation is a crude lysate of a cell, the cell comprising a recombinant nucleic acid that encodes the 2,4-D α-ketoglutarate dioxygenase.

32. A kit according to claim 27 wherein the dried enzyme preparation is immobilized on a solid support.

33. A kit according to claim 32 wherein the solid support is selected from the group consisting of a bead and a dipstick.

34. A kit for detecting the presence of a phenoxy ether compound in a sample, the kit comprising:

a dried enzyme preparation immobilized on a solid support, the dried enzyme preparation comprising a 2,4-D α-ketoglutarate dioxygenase having an activity when hydrated of cleaving a phenoxy ether bond of the compound to produce a phenolic product and that maintains the activity after storage at approximately 20° C. for at least three months;

$Fe(NH_4)_2(SO_4)_2$;

α-ketoglutarate;

4-aminoantipyrine;

potassium ferricyanide; and instructions for use.

35. A kit according to claim 34 wherein the solid support is selected from the group consisting of a bead and a dipstick.

36. A kit for detecting the presence of a phenoxy ether compound in a sample, the kit comprising:

a dried enzyme preparation immobilized on a solid support, the dried enzyme preparation comprising a 2,4-D α-ketoglutarate dioxygenase having an activity when hydrated of cleaving a phenoxy ether bond of the compound to produce a phenolic product and that maintains the activity after storage at approximately 20° C. for at least three months;

an aqueous 5 mM $Fe(NH_4)_2(SO_4)_2$ solution;

an aqueous 100 mM α-ketoglutarate solution;

an aqueous 40 mM 4-aminoantipyrine solution;

an aqueous 8% wt/vol potassium ferricyanide solution;

an aqueous pH 8.0 buffer solution; and instructions for use.

* * * * *

UNITED STATES PATENT AND TRADEMARK OFFICE
CERTIFICATE OF CORRECTION

PATENT NO. : 5,656,422

DATED : August 12, 1997

INVENTOR(S) : CRAWFORD ET AL.

It is certified that error appears in the above-identified patent and that said Letters Patent is hereby corrected as shown below:

Column 3, line 1, "Curacton®" should be --Curacron®--.

Column 3, line 2, "Bolstare" should be --Bolstar®--.

Column 4, line 24, "shows" should be --show--.

Column 6, line 50, "Pseudomonas, Moraxelia, and Xanthomonas" should be --*Pseudomonas, Moraxella,* and *Xanthomonas*--.

Column 7, line 51, "O-(2-isopropyl-4-methyl-6-pyrimidinyl)" should be -- *o*-(2-isopropyl-4-methyl-6-pyrimidinyl) --.

Column 7, line 66, "Karatbane®" should be --Karathane®--.

Column 12, line 14, "Join" should be --join--.

Column 12, line 28, "Synthesized" should be --synthesized--.

Column 13, line 8, "arian" should be --avian--.

Column 14, line 42, "PAOpb 1pk (pRO103)" should be --PAO1(pRO103)--.

Column 14, line 48, "SIC" should be --SK$^+$--.

Column 16, line 9, ".gel" should be --gel--.

Column 16, line 33, "ID$_{560}$" should be --OD$_{560}$--.

Column 16, line 39, "bypassing" should be --by passing--.

Column 16, line 61, "pAO1" should be --PAO1--.

Column 17, line 27, the hyphen "-" should be deleted after --(pRO103)--.

UNITED STATES PATENT AND TRADEMARK OFFICE
CERTIFICATE OF CORRECTION

PATENT NO. : 5,656,422

DATED : August 12, 1997

INVENTOR(S) : CRAWFORD ET AL.

It is certified that error appears in the above-identified patent and that said Letters Patent is hereby corrected as shown below:

Column 17, line 41, "pAO1" should be --PAO1--.

Column 19, line 21, "(DYG3)" should be --(pYG3)--.

Figure 13B:
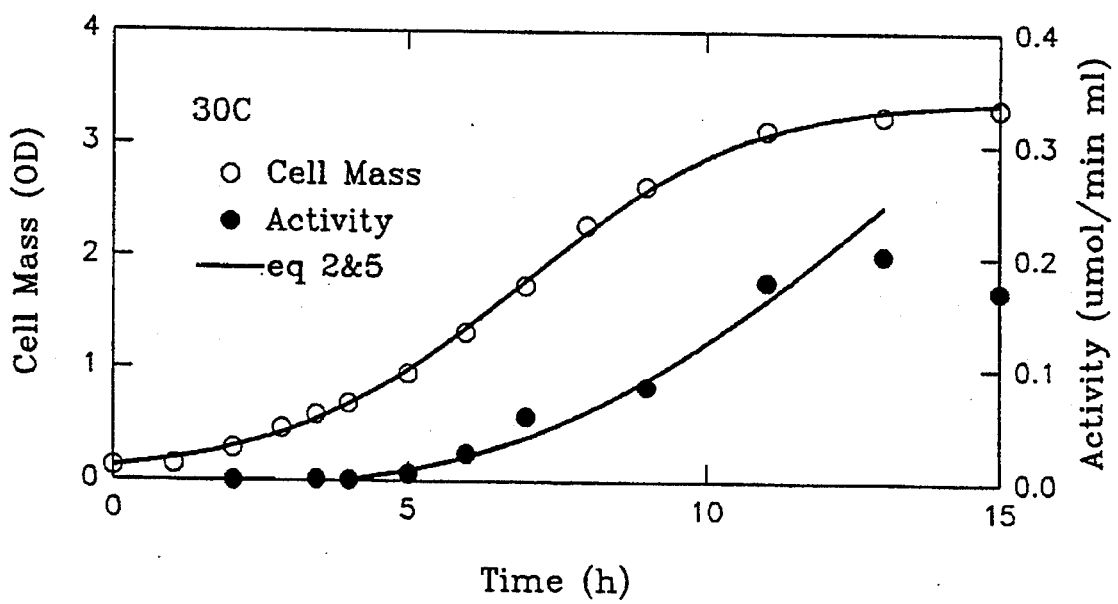

Column 20, line 60, "FIGS. 13A nd 13B" should be --FIGS. 13A and 13B--.

Column 20, line 66, "pYG3)" should be --(pYG3)--.

Column 21, line 8, "(at)" should be --($\Delta$t)--.

Column 21, line 30, "Changed" should be --changed--.

Column 22, line 24, "The concentration" should be --The saturation concentration--.

Column 23, line 66, "(-20°C.)" should be --(~20°C)--.

Column 27, lines 28-29, "2,6-dichloro-2-methoxy/benzoic acid" should be -- 2,6-dichloro-2-methoxy-benzoic acid --.

Signed and Sealed this

Fifteenth Day of December, 1998

Attest:

BRUCE LEHMAN

*Attesting Officer*  *Commissioner of Patents and Trademarks*